US010646154B2

(12) United States Patent
Merchant-Borna et al.

(10) Patent No.: US 10,646,154 B2
(45) Date of Patent: May 12, 2020

(54) SYSTEM AND METHOD TO ASSESS RISK OF CHANGES TO BRAIN WHITE MATTER BASED ON HEAD IMPACT DOSE EQUIVALENT NUMBER

(71) Applicants: Kian Merchant-Borna, Rochester, NY (US); Jeffrey J. Bazarian, Honeoye Falls, NY (US)

(72) Inventors: Kian Merchant-Borna, Rochester, NY (US); Jeffrey J. Bazarian, Honeoye Falls, NY (US)

(73) Assignee: University of Rochester, Rochester, NY (US)

( * ) Notice: Subject to any disclaimer, the term of this patent is extended or adjusted under 35 U.S.C. 154(b) by 247 days.

(21) Appl. No.: 15/539,790

(22) PCT Filed: Jan. 7, 2016

(86) PCT No.: PCT/US2016/012486
§ 371 (c)(1),
(2) Date: Jun. 26, 2017

(87) PCT Pub. No.: WO2016/112189
PCT Pub. Date: Jul. 14, 2016

(65) Prior Publication Data
US 2018/0014771 A1 Jan. 18, 2018

Related U.S. Application Data

(60) Provisional application No. 62/101,786, filed on Jan. 9, 2015.

(51) Int. Cl.
*A61B 5/00* (2006.01)
*A61B 5/11* (2006.01)
(Continued)

(52) U.S. Cl.
CPC ............ *A61B 5/4064* (2013.01); *A42B 3/046* (2013.01); *A42B 3/0433* (2013.01);
(Continued)

(58) Field of Classification Search
CPC ....... A61B 5/11; A61B 5/4064; A61B 5/6814; A61B 5/6803; A61B 5/7275; A61B 5/7278; A42B 3/046; A42B 3/0433
See application file for complete search history.

(56) References Cited

U.S. PATENT DOCUMENTS 6,826,509 B2   11/2004   Crisco, III et al.
8,554,509 B2   10/2013   Crisco, III et al.
(Continued)

OTHER PUBLICATIONS

ISA/US International Search Report and Written Opinion for Corresponding International Application No. PCT/US16/12486, dated Mar. 14, 2016 (15 pgs).
(Continued)

*Primary Examiner* — Max F Hindenburg
(74) *Attorney, Agent, or Firm* — Harris Beach PLLC

(57) ABSTRACT

A system to assess risk of changes to brain white matter includes a sensor system adapted to measure an energy of each impact to an individual belonging to a sub-population that causes a repetitive head impact (RHI). A head impact dose equivalent number (HIDEN) process calculates a HIDEN for a most recent RHI event based on the energy of the most recent RHI event, a time of the most recent RHI, and all previously recorded RHI events available in a non-volatile memory. A sub-population function process calculates a risk assessment number based on the sub-population and the HIDEN. A risk assessment notification means provides a notification of the risk assessment number. A method to assess risk of changes to brain white matter based on a head impact dose equivalent number and a
(Continued)

method to define a sub-population function to convert a HIDEN to a risk assessment value is also described.

30 Claims, 26 Drawing Sheets

(51) Int. Cl.
A42B 3/04 (2006.01)
A61B 5/055 (2006.01)

(52) U.S. Cl.
CPC ............ *A61B 5/0002* (2013.01); *A61B 5/055* (2013.01); *A61B 5/11* (2013.01); *A61B 5/6803* (2013.01); *A61B 5/6814* (2013.01); *A61B 5/7275* (2013.01); *A61B 5/7282* (2013.01)

(56) References Cited

U.S. PATENT DOCUMENTS

| | | | |
|---|---|---|---|
| 8,797,165 B2 | 8/2014 | Greenwald et al. | |
| 2009/0000377 A1* | 1/2009 | Shipps | A61B 5/11 73/514.16 |
| 2011/0125063 A1 | 5/2011 | Shalon et al. | |
| 2012/0304367 A1* | 12/2012 | Howard | A42B 3/046 2/413 |
| 2013/0232667 A1* | 9/2013 | Leon | A42B 3/12 2/411 |
| 2014/0039355 A1 | 2/2014 | Crisco, III et al. | |
| 2014/0149067 A1 | 5/2014 | Merril et al. | |
| 2014/0192326 A1 | 7/2014 | Kiderman et al. | |
| 2015/0040665 A1* | 2/2015 | Borkholder | A61B 5/002 73/510 |
| 2015/0080766 A1* | 3/2015 | Ji | A61B 5/11 600/595 |
| 2016/0262694 A1* | 9/2016 | Calcano | A61L 2/16 |

OTHER PUBLICATIONS

Engsberg, Jr, et al., "Spinal cord and brain injury protection; testing concept for a protective device", 2009, Spinal Cord, vol. 47 (pp. 634-639).
Force Impact Technologies LLC, et al., Announcing New Head Injury Awareness Mouthguard, Oct. 20, 2014 (2 pgs.).
Davenport, Elizabeth M., et al., "Abnormal White Matter Integrity Related to Head Impact Exposure in a Season of High School Varsity Football," 2014, Journal of Neurotrauma, vol. 31 (pp. 1617-1624).
Murugavel, Murali, et al., "A Longitudinal Diffusion Tensor Imaging Study Assessing White Matter Fiber Tracts after Sports Related Concussion," 2014, Journal of Neurotrauma, vol. 31 (pp. 1-12).
Henn, Hans-Wolfgang, "Crash Tests and the Head Injury Criterion," 1998, Teaching Mathematics and Its Applications, vol. 17 (pp. 162-170).
Camarillo, David B., et al., "An Instrumented Mouthguard for Measuring Linear and Angular Head Impact Kinematics in American Football," 2013, Annals of Biomedical Engineering, vol. 41 (pp. 1-21).
Blumbergs, P. C., et al., "Staining of amyloid precursor protein to study axonal damage in mild head injury," 1994, The Lancet, vol. 344 (pp. 1055-1056).
Buki, A., et al., "All roads lead to disconnection?—Traumatic axonal injury revisited," 2006, Acta Neurochirurgica, vol. 148 (pp. 181-195).
Bazarian, Jeffrey J., et al., "Bench to Bedside: Evidence for Brain Injury after Concussion—Looking beyond the Computed Tomography Scan," 2006, Academic Emergency Medicine, vol. 13 (pp. 199-214).
Hixson, James E., et al., "Restriction isotyping of human apolipoprotein E by gene amplification and cleavage with Hhal," 1990, Journal of Lipid Research, vol. 31 (pp. 545-548).

Collins, Michael W., et al., "On-Field Predictors of Neuropsychological and Symptom Deficit Following Sports-related Concussion," 2003, Clinical Journal of Sport Medicine, vol. 13 (pp. 222-229).
Saczynski, Jane S., et al., "The Relation between Apolipoprotein A-I Dementia: The Honolulu-Asia Aging Study," 2007, American Journal of Epidemiology, vol. 165 (pp. 985-992).
Merched, A., et al., "Decreased high-density lipoprotein cholesterol and serum apolipoprotein Al concentrations are highly correlated with the severity of Alzheimer's disease," 2000, Neurobiology of Aging, vol. 21 (pp. 27-30).
Craig-Schapiro, Rebecca, et al., "Multiplexed Immunoassay Panel Identifies Novel CSF Biomarkers for Alzheimer's Disease Diagnosis and Prognosis," 2011, PLoS ONE, vol. 6 (pp. 1-15).
Perrin, Richard J., et al., "Multi-modal techniques for diagnosis and prognosis of Alzheimer's disease," 2009, Nature, vol. 461 (pp. 916-922).
Marchi, Nicola, et al., "Consequences of Repeated Blood-Brain Barrier Disruption in Football Players," 2013, PLoS ONE, vol. 8 (pp. 1-11).
Wang, Jiaqiong, et al., "Traumatic Axonal Injury in the Optic Nerve: Evidence for Axonal Swelling, Disconnection, Dieback, and Reorganization," 2011, Journal of Neurotrauma, vol. 28 (pp. 1185-1198).
Sulaiman, Ahmed Mohammed, et al., "Stereology and Ultrastructure of Chronic Phase Axonal and Cell Soma Pathology in Stretch-Injured Central Nerve Fibers," 2011, Journal of Neurotrauma, vol. 28 (pp. 383-400).
Kou, Zhifeng, et al., "The Role of Advanced MR Imaging Findings as Biomarkers of Traumatic Brain Injury," 2010, J Head Trauma Rehabil., vol. 25 (pp. 267-282).
Unterberg, A. W., et al., "Edema and Brain Trauma," 2004, Neuroscience, vol. 129 (pp. 1021-1029).
Bazarian, Jeffrey J., et al., "Diffusion Tensor Imaging Detects Clinically Important Axonal Damage After Mild Traumatic Brain Injury: A Pilot Study," 2007, Journal of Neurotrauma, vol. 24 (pp. 1447-1459).
Mayer, A.R., et al., "A prospective diffusion tensor imaging study in mild traumatic brain injury," 2010, Neurology, vol. 74 (pp. 643-650).
Henry, Luke C., et al., "Acute and Chronic Changes in Diffusivity Measures after Sports Concussion," 2011, Journal of Neurotrauma, vol. 28 (pp. 2049-2059).
MacDonald, Christine L., et al., "Diffusion Tensor Imaging Reliably Detects Experimental Traumatic Axonal Injury and Indicates Approximate Time of Injury," 2007, Journal of Neuroscience, vol. 27 (pp. 1-19).
Sun, Daniel, et al., "Structural Remodleing of Fibrous Astrocytes after Axonal Injury," 2010, Journal of Neuroscience, vol. 30 (pp. 1-24).
Csuka, Esther, et al., "Cell activation and inflammatory response following traumatic axonal injury in the rat," 2000, NeuroReport, vol. 11 (pp. 2587-2590).
Harris, Neil G., et al., "Pericontusion Axon Sprouting is Spatially and Temporally Consistent With a Growth-Permissive Environment after Traumatic Brain Injury," 2010, Journal of Neuropathology & Experimental Neurology, vol. 69 (pp. 1-25).
Budde, Matthew D., et al., "The contributn of gliosis to diffusion tensor anisotropy and tractography following traumatic brain injury: validation in the rat using Fourier analysis of stained tissue sections," 2011, Brain, vol. 134 (pp. 2248-2260).
Bouix, Sylvain, et al., "Increased Gray Matter Diffusion Anisotropy in Patients with Persistent Post-Concussive Symptoms following Mild Traumatic Brain Injury," 2013, PLoS ONE, vol. 8 (pp. 1-9).
Shenton, ME, et al. "A Review of Magnetic Resonance Imaging and Diffusion Tensor Imaging Findings in Mild Traumatic Brain Injury," 2012, Brain Imaging & Behavior, vol. 6 (pp. 1-70).
Li, Shangxun, et al., "Temporal profiles of axonal injury following impact acceleration traumatic brain injury in rats—a comparative study with diffusion tensor imaging and morphological analysis," 2013, Int J Legal Med., vol. 127 (pp. 159-167).
Gons, Rob A.R., et al., "Physical activity is related to the structural integrity of cerebral white matter," 2013, Neurology, vol. 81 (pp. 971-976).

(56) References Cited

OTHER PUBLICATIONS

Hayes, Wilson C., et al., "Forensic Injury Biomechanics, 2007, Annual Review of Biomedical Engineering," vol. 9 (pp. 55-86).
Riemann, Bryan L., et al., "Assessment of Mild Head Injury Using Measures of Balance and Cognition: A Case Study," 1997, Journal of Sport Rehabilitation, vol. 6 (pp. 283-289).
Finnoff, Jonathan T., et al., "Intrarater and Interrater Reliability of the Balance Error Scoring System (BESS)," 2009, PM&R vol. 1 (pp. 50-54).
Clark, Ross A., et al., "Validity and reliability of the Nintendo Wii Balance Board for assessment of standing balance," 2010, Gait & Posture, vol. 31 (pp. 307-310).
Zhang, Yajing, et al., "Atlas-Guided Tract Reconstruction for Automated and Comprehensive Examination of the White Matter Anatomy," 2010, Neuroimage, vol. 52 (pp. 1-26).
Whitcher, Brandon, et al., "Using the Wild Bootstrap to Quantify Uncertainty in Diffusion Tensor Imaging," 2008, Human Brain Mapping, vol. 29 (pp. 346-362).
Zhu, Tong, et al., "An optimized wild bootstrap method for evaluation of measurement uncertainties of DTI-derived parameters in human brain," 2008, NeuroImage, vol. 40 (pp. 1144-1156).
Jones, Derek K., et al., "The effect of filter size on VBM analyses of DT-MRI data," 2005, NeuroImage, vol. 26 (pp. 546-554).
Nichols, Thomas E., et al., "Nonparametric Permutation Tests for Functional Neuroimaging: A Primer with Examples," 2001, Human Brain Mapping, vol. 15 (pp. 1-25).
Cantu R, Nowinski C. Sports Legacy Institute, Hit Count Initiative. http://www.sportslegacy.org/policy/hit-count/. Feb. 2012;Last accessed Nov. 24, 2013.
Langlois, Jean A., "The Epidemiology and Impact of Traumatic Brain Injury," 2006, Journal of Head Trauma Rehabilitation, vol. 21 (pp. 375-378).
Greenwald, Richard M., et al., "Head Impact Severity Measures for Evaluating Mild Traumatic Brain Injury Risk Exposure," 2008, Neurosurgery, vol. 62 (pp. 789-798).
Crisco, Joseph J., et al., "Frequency and Location of Head Impact Exposures in Individual Collegiate Football Players," 2010, Journal of Athletic Training, vol. 45 (pp. 549-559).
Broglio, Steven P., et al., "The Biomechanical Properties of Concussions in High School Football," 2010, Medicine & Science in Sports & Exercise, vol. 42 (pp. 2064-2071).
Marar, Mallika, et al., "Epidemiology of Concussions Among United States High School Athletes in 20 Sports," 2012, The American Journal of Sports Medicine, vol. 40 (pp. 747-755).
Meehan, III, M.D., William P., et al., "Assessment and Management of Sport-Related Concussions in United States High Schools," 2011, Am J Sports Med., vol. 39 (pp. 2304-2310).
McCrory, Paul, et al., "The Evidence for Chronic Traumatic Encephalopathy in Boxing," 2007, Sports Medicine, vol. 37 (pp. 467-476).
Zetterberg, MD, PhD, Henrik, et al., "Neurochemical Aftermath of Amateur Boxing," 2006, Archives of Neurology, vol. 63 (pp. 1277-1280).
Talavage, Thomas M., et al., "Functionally-Detected Cognitivie Impairment in High School Football Players without Clinically-Diagnosed Concussion," 2014, Journal of Neurotrauma, vol. 31 (pp. 327-338).
Breedlove, Evan L., et al., "Biomechanical correlates of symptomatic and asymptomatic neurophysiological impairment in high school football," 2012, Journal of Biomechanics (pp. 1265-1272).
Jantzen, PhD, Kelly J., "Functional Magnetic Resonance Imaging of Mild Traumatic Brain Injury," 2010, Journal of Head Trauma Rehabilitation, vol. 25 (pp. 256-266).
McAllister, Md., T.W., et al., "Cognitivie effects of one season of head impacts in a cohort of collegiate contact sport athletes," 2012, Neurology, (pp. 1777-1784).
Martland, M.D., Harrison S., et al., "Punch Drunk," 1928, JAMA, vol. 91 (pp. 1103-1107).
McKee, MD, Ann C., et al., Chronic Traumatic Encephalopathy in Athletes: Progressive Tauopathy following Repetitive Head Injury, "2009, Journal of Neuropathology & Experimental Neurology," vol. 68 (pp. 709-735).
Omalu, Bennet, et al., "Emerging Histomorphologic Phenotypes of Chronic Traumatic Encephalopathy in American Athletes," 2011, Neurosurgery, vol. 69 (pp. 173-183).
Baugh, Christine M., et al., "Chronic traumatic encephalopathy: neurodegeneration following repetitive concussive and subconcussive brain trauma," 2012, Brain Imaging and Behavior, vol. 6 (pp. 244-254).
McKee, Ann C., et al., "The spectrum of disease in chronic traumatic encephalopathy," 2013, Brain, vol. 136 (pp. 43-64).
McRea, Michael, et al., "Unreported Concussion in High School Football Players Implications for Prevention," 2004, Clin J Sport Med., vol. 14 (pp. 13-17).
Spiotta, Alejandro M., et al., "Subconcussive Impact in Sports; A New Era of Awareness," 2011, World Neurosurgery, vol. 75 (pp. 175-178).
Hazrati, Lili-Naz, et al., "Absence of chronic traumatic encephalopathy in retired football players with multiple concussions and neurological symptomatology," 2013, Frontiers in Human Neuroscience, vol. 7 (pp. 1-9).
Stern, Robert A., et al., "Long-term Consequences of Repetitive Brain Trauma: Chronic Traumatic Encephalopathy," 2011, American Academy of Physical Medicine and Rehabilitation, vol. 3 (pp. S460-S467).
Zhang, L., et al., "Diffusion Anisotropy Changes in the Brains of Professional Boxers," 2006, American Journal of Neuroradiology, vol. 27 (pp. 2000-2004).
Koerte, Inga K., et al., "A prospective study of physician-observed concussion during a varsity university hockey season: white matter integrity in ice hockey players. Part 3 of 4," 2012, Neurosurgical Focus, vol. 33 (pp. 1-7).
McAllister, Thomas W., et al., "Effect of head impacts on diffusivity measures in a cohort of collegiate contact sport athletes," 2014, Neurology, vol. 82 (pp. 63-69).
Bazarian, Jeffrey J., et al., "Subject-Specific Changes in Brain Whie Matter on Diffusion Tensor Imaging After Sports-Related Concussion," 2012, Magnetic Resonance Imaging, vol. 30 (pp. 171-180).
Fujita, Motoki, et al., "Intensity-and Interval-Specific Repetitive Traumatic Brain Injury Can Evoke Both Axonal and Microvascular Damage," 2012, Journal of Neurotrauma, vol. 29 (pp. 2172-2180).
Mihalik, Jason P., et al., "Measurement of Head Impacts in Collegiate Football Players: An Investigation of Positional and Event-Type Differences," 2007, Neurosurgery, vol. 61 (pp. 1229-1235).
Corrigan, John D., et al., "Initial Reliability and Validity of the Ohio State University TBI Identification Method," 2007, J Head Trauma Rehabil., vol. 22 (pp. 318-329).
Blumbergs, Peter C., et al., "Topography of Axonal Injury as Defined by Amyloid Precursor Protein and the Sector Scoring Method in Mild and Severe Closed Head Injury," 1995, Journal of Neurotrauma, vol. 12 (pp. 565-572).

\* cited by examiner

PERCENT OF WHITE MATTER WITH SIGNIFICANTLY INCREASED MD

PERCENT OF WHITE MATTER WITH SIGNIFICANTLY DECREASED MD

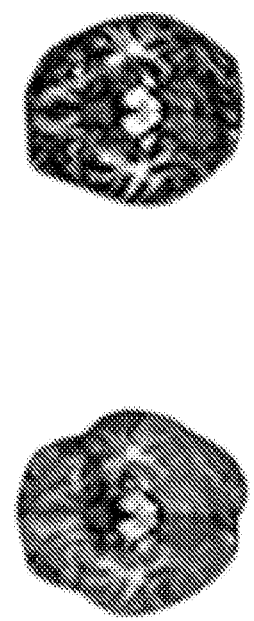
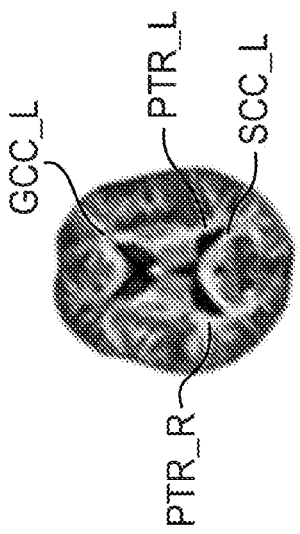
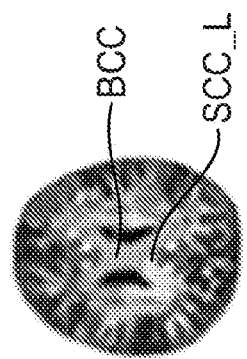
FIG. 7B
HEALTHY CONTROL
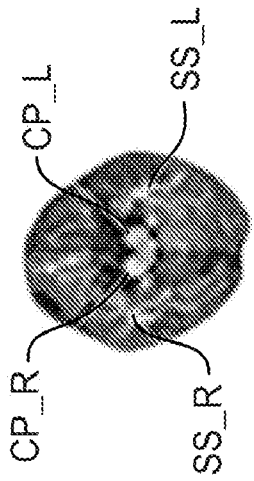
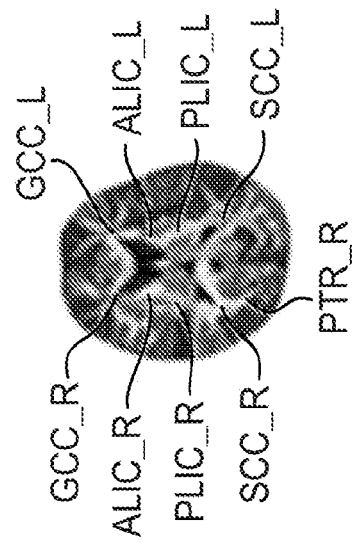
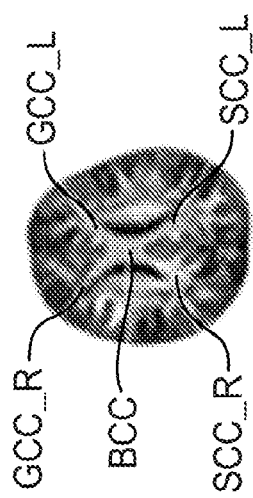
FIG. 7A
FOOTBALL PLAYER TABLE 1. BASELINE COMPARISON OF ATHLETE (n = 10) AND CONTROL (n = 5) SUBJECTS.

| PARAMETER | ATHLETES MEAN | (SD) | CONTROLS MEAN | (SD) | p-VALUE |
|---|---|---|---|---|---|
| AGE (YEARS) | 20.4 | (1.08) | 20.6 | (1.14) | 0.81 |
| BODY MASS INDEX (kg/m2) | 30.74 | (1.58) | 24.22 | (2.02) | 0.03 |
| CLINICAL CORRELATES | | | | | |
| PHYSIOLOGIC MEASURES | | | | | |
| ApoE4 Positive, n (%) | 2 | (20.00) | 2 | (40.00) | 0.56 |
| ApoA1 (mg/dL) | 122.5 | (8.01) | 149.2 | (10.42) | 0.07 |
| S100B (ug/L) | 0.107 | (0.03) | 0.059 | (0.01) | 0.34 |
| S100B AutoAb Titer (Abs) | 1.11 | (0.27) | 2.52 | (0.06) | 0.01 |
| BALANCE | | | | | |
| BALANCE ERROR SCORING SYSTEM | 17.1 | (4.70) | 13.4 | (5.30) | 0.19 |
| CENTER OF PRESSURE TOTAL PATH LENGTH (cm) | 288.6 | (33.00) | 342.2 | (132.00) | 0.23 |
| COGNITIVE PERFORMANCE | | | | | |
| VISUAL MEMORY SCORE | 74.3 | (15.10) | 70.2 | (14.60) | 0.63 |
| VERBAL MEMORY SCORE | 90.4 | (6.20) | 85.6 | (9.70) | 0.26 |
| VISUAL MOTOR SPEED SCORE | 47.2 | (6.10) | 43.8 | (6.20) | 0.33 |
| REACTION TIME (SEC) | 0.49 | (0.05) | 0.52 | (0.04) | 0.17 |
| IMPULSE CONTROL | 3.0 | (4.10) | 6.6 | (2.10) | 0.04 |
| SYMPTOM | 0.20 | (0.63) | 3.20 | (5.20) | 0.09 |
| COGNITIVE EFFICIENCY SCORE | 0.45 | (0.12) | 0.39 | (0.11) | 0.40 |

FIG. 10

TABLE 2. HELMET IMPACT MEASURES AMONG ATHLETE SUBJECTS (n=10)

| POSITION | TOTAL HEAD HITS | MEAN (SD) LINEAR ACCELERATION / HITS (g) | MEAN (SD) ROTATIONAL ACCELERATION / HITS (rad/sec$^2$) | TOTAL LINEAR ACCELERATION (g) | TOTAL ROTATIONAL ACCELERATION (rad/sec$^2$) |
|---|---|---|---|---|---|
| RUNNING BACK | 431 | 29.78 (20) | 1880.53 (1513) | 12,836.0 | 810,511 |
| TIGHT END | 572 | 31.41 (20) | 1815.66 (1279) | 18,033.0 | 1,042,191 |
| LINEBACKER | 612 | 37.53 (25) | 1973.65 (1438) | 22,969.3 | 1,207,879 |
| DEFENSIVE LINE | 617 | 27.09 (14) | 1704.77 (1034) | 16,742.4 | 1,053,554 |
| DEFENSIVE LINE | 649 | 28.23 (17) | 1691.95 (1216) | 18,325.1 | 1,098,081 |
| FULL BACK | 1,042 | 31.84 (22) | 1877.13 (1572) | 33,250.3 | 1,959,725 |
| LINEBACKER | 1,142 | 35.24 (24) | 2071.71 (1578) | 40,245.5 | 2,365,894 |
| DEFENSIVE LINE | 1,423 | 34.36 (20) | 2021.55 (1188) | 48,903.4 | 2,876,675 |
| OFFENSIVE TACKLE | 1,431 | 26.91 (14) | 1726.87 (1026) | 38,516.7 | 2,471,157 |
| CENTER | 1,850 | 31.88 (18) | 1837.52 (1076) | 58,994.1 | 3,399,421 |

FIG. 11

TWO EXAMPLES, BOTH WITH A SIMILAR PROFILE OF FORCES SUSTAINED TO THE HEAD, BUT DIFFER IN THE TIMING OF EXPOSURE

| | F | G | WEIGHTED VALUE | WEIGHTED VALUE FORMULA |
|---|---|---|---|---|
| | TIME SINCE PRIOR HIT (SECONDS) | LINEARACC | | |
| | 0.000 | 32.98 | 32.98 | =G2 |
| | 541.000 | 32.44 | 32.50 | =G3+(G2*(1/F3)) |
| | 661.000 | 42.00 | 42.08 | =G4+(G3*(1/F4))+(G2*(1/SUM(F3:F4)) |
| | 512.000 | 29.21 | 29.34 | =G5+(G4*(1/F5))+(G3*(1/SUM(F4:F5)))=(G2*(1/SUM(F3:F5))) |
| | 1053.928 | 35.74 | 35.82 | =G6+(G5*(1/F6))+(G4*(1/SUM(F5:F6)))+(G3*(1/SUM(F4:F6)))+(G2*(1/SUM(F3:F6))) |
| | 754.660 | 35.80 | 35.90 | =G7+(G6*(1/F7))+(G5*(1/SUM(F6:F7)))+(G4*(1/SUM(F5:F7)))+(G3*(1/SUM(F4:F7)))+(G2*(1/SUM(F3:F7))) |
| | | 208.17 | 208.62 | =SUM(H2:H7) TIME BETWEEN HITS – WEIGHTED VALUE |

SAME PROFILE OF EXPOSURE TO FORCE (g)

TIMING VARIES

| | F | G | WEIGHTED VALUE | WEIGHTED VALUE FORMULA |
|---|---|---|---|---|
| | TIME SINCE PRIOR HIT (SECONDS) | LINEARACC | | |
| | 0.000 | 32.98 | 32.98 | =G2 |
| | 0.978 | 32.44 | 66.16 | =G3+(G2*(1/F3)) |
| | 0.500 | 42.00 | 129.20 | =G4+(G3*(1/F4))+(G2*(1/SUM(F3:F4)) |
| | 0.200 | 29.21 | 305.21 | =G5+(G4*(1/F5))+(G3*(1/SUM(F4:F5)))=(G2*(1/SUM(F3:F5))) |
| | 2.400 | 35.74 | 82.61 | =G6+(G5*(1/F6))+(G4*(1/SUM(F5:F6)))+(G3*(1/SUM(F4:F6)))+(G2*(1/SUM(F3:F6))) |
| | 0.590 | 35.80 | 135.16 | =G7+(G6*(1/F7))+(G5*(1/SUM(F6:F7)))+(G4*(1/SUM(F5:F7)))+(G3*(1/SUM(F4:F7)))+(G2*(1/SUM(F3:F7))) |
| | | 208.17 | 751.32 | =SUM(H2:H7) TIME BETWEEN HITS – WEIGHTED VALUE |

FIG. 12

| | | | | | | |
|---|---|---|---|---|---|---|
| LA | 0.58 | 0.34 | 0.235 | -0.68 | 0.46 | 0.114 |
| RA | 0.60 | 0.36 | 0.215 | -0.77 | 0.59 | 0.045 |
| HIC15 | 0.58 | 0.33 | 0.241 | 0.72 | 0.51 | 0.081 |
| GSI | 0.56 | 0.32 | 0.266 | 0.69 | 0.48 | 0.103 |
| HITsp | 0.62 | 0.38 | 0.184 | -0.76 | 0.58 | 0.049 |
| LA | 0.68 | 0.47 | 0.027 | -0.82 | 0.67 | 0.002 |
| RA | 0.56 | 0.32 | 0.091 | -0.65 | 0.42 | 0.041 |
| HIC15 | 0.70 | 0.49 | 0.023 | -0.84 | 0.71 | 0.001 |
| GSI | 0.73 | 0.54 | 0.013 | -0.88 | 0.77 | 0.000 |
| HITsp | 0.58 | 0.33 | 0.083 | -0.70 | 0.49 | 0.023 |
| LA | 0.66 | 0.43 | 0.139 | -0.78 | 0.61 | 0.038 |
| RA | 0.61 | 0.37 | 0.202 | -0.78 | 0.60 | 0.040 |
| HIC15 | 0.59 | 0.35 | 0.224 | -0.84 | 0.70 | 0.015 |
| GSI | 0.63 | 0.40 | 0.168 | -0.85 | 0.73 | 0.011 |
| HITsp | 0.60 | 0.36 | 0.215 | -0.72 | 0.52 | 0.074 |

TABLE AND FIGURES

TABLE 1. MEAN (RANGE) HELMET IMPACT METRICS FOR 10 ATHLETE SUBJECTS

| | METRIC | MEAN | RANGE |
|---|---|---|---|
| MEAN, NON-CUMULATIVE | LA | 31 | (26 – 38) |
| | RA | 1,860 | (1,692 – 2,072) |
| | $HIC_{15}$ | 20 | (11 – 33) |
| | GSI | 32 | (18 – 53) |
| | HITsp | 18 | (16 – 20) |
| PEAK, NON-CUMULATIVE | LA | 147 | (98 – 180) |
| | RA | 10,479 | (7,612 – 16,661) |
| | $HIC_{15}$ | 536 | (184 – 777) |
| | GSI | 888 | (356 – 1,457) |
| | HITsp | 118 | (62 – 199) |
| CUMULATIVE, UNWEIGHTED | LA | 30,882 | (12,836 – 58,994) |
| | RA | 1,828,509 | (810,512 – 3,399,421) |
| | $HIC_{15}$ | 19,622 | (7,411 – 35,397) |
| | GSI | 31,033 | (11,606 – 56,998) |
| | HITsp | 17,358 | (7,239 – 32,701) |
| CUMULATIVE, WEIGHTED FOR TBH | LA | 1.9E+9 | (8.1E+8 – 3.2E+9) |
| | RA | 1.1E+11 | (4.8E+10 – 2.0E+11) |
| | $HIC_{15}$ | 1.5E+9 | (5.0E+8 – 3.5E+9) |
| | GSI | 2.4E+9 | (8.0E+8 – 5.6E+9) |
| | HITsp | 1.0E+9 | (4.4E+8 – 1.9E+9) |
| CUMULATIVE, WEIGHTED FOR TUA | LA | 1,172 | (296 – 2,098) |
| | RA | 69,938 | (19,571 – 133,996) |
| | $HIC_{15}$ | 730 | (189 – 1,495) |
| | GSI | 1,140 | (281 – 2,362) |
| | HITsp | 663 | (167 – 1,323) |
| CUMULATIVE, WEIGHTED FOR TBH & TUA | LA | 8.1E+7 | (2.5E+7 – 2.3E+8) |
| | RA | 5.0E+9 | (1.3E+9 – 1.5E+10) |
| | $HIC_{15}$ | 6.4E+7 | (1.5E+7 – 2.3E+8) |
| | GSI | 1.0E+8 | (2.4E+7 – 3.8E+8) |
| | HITsp | 4.4E+7 | (1.3E+7 – 1.3E+8) |

UNITS FOR LA ARE IN g's AND FOR RA ARE $rad/sec^2$; OTHER METRICS ARE UNITLESS. LA (LINEAR ACCELERATION, IN UNITS OF GRAVITATIONAL ACCELERATION (g), RA (ROTATIONAL ACCELERATION, IN UNIT OF RADIANS PER SECOND SQUARED). GADD SEVERITY INDEX (GSI), HEAD INJURY CRITERION (HIC), HEAD IMPACT TECHNOLOGY SUSPECT PROFILE (HITsp).

FIG. 16

SYSTEM AND METHOD TO ASSESS RISK OF CHANGES TO BRAIN WHITE MATTER BASED ON HEAD IMPACT DOSE EQUIVALENT NUMBER

CROSS-REFERENCE TO RELATED APPLICATIONS

This application is a national stage application under 35 U.S.C. § 371 of PCT Application No. PCT/US2016/12486, filed Jan. 7, 2016, SYSTEM AND METHOD TO ASSESS RISK OF CHANGES TO BRAIN WHITE MATTER BASED ON HEAD IMPACT DOSE EQUIVALENT NUMBER published as WO 2016/112189, which claims priority to and the benefit of U.S. provisional patent application Ser. No. 62/101,786, SYSTEM AND METHOD TO ASSESS RISK OF CHANGES TO BRAIN WHITE MATTER BASED ON HEAD IMPACT DOSE EQUIVALENT NUMBER, filed Jan. 9, 2015, which applications are incorporated herein by reference in their entirety.

FIELD OF THE APPLICATION

The application relates to impact-related changes to human brain white matter and particularly, to systems and methods for mitigating changes and injury to brain white matter as a result of repetitive head impacts.

BACKGROUND

In recent years there has been an increasing awareness of long term or chronic effects resulting from concussions and traumatic brain injury.

One area of intensive military research into head trauma results from the unfortunate consequences of asymmetric warfare of the twenty-first century and its wide spread use of improvised explosive devices (IED) that makes head trauma and brain injury among combatants all too common now. Another rapidly emerging area of study relates to concussions suffered in sports activities. Beginning with an awareness of chronic brain injury to boxers, this field of research quickly extended to U.S. professional football and the national football league (NFL™).

Combined with the new national push for more brain research, these seemingly disparate areas of head injury are combining into a study and search for better a understanding of how to study brain injury and the chronic after effects caused by brain injury.

SUMMARY

According to one aspect, a system to assess risk of changes to brain white matter based on a head impact dose equivalent number includes a sensor system adapted to directly or indirectly measure an energy of each impact to at least one individual that causes a repetitive head impact (RHI). The at least one individual belongs to a sub-population. A clock means is configured to provide a time. A computer is communicatively coupled to the sensor system or to a non-volatile memory having stored thereon data from the sensor system to estimate an energy of each RHI event, and communicatively coupled to the clock means to associate thereto each energy of each RHI event a RHI time stamp and to record a time stamped energy for each RHI event. A head impact dose equivalent number (HIDEN) process runs on the computer. The HIDEN process calculates a HIDEN for a most recent RHI event based on the energy of the most recent RHI event, a time of the most recent RHI, and all previously recorded RHI events available in a non-volatile memory. Each RHI event of all previously recorded RHI events is time weighted by the time between each of the all previously recorded RHI events and the time of the most recent RHI. A sub-population function process runs on the computer or on another computer communicatively coupled to the computer. The sub-population function process is configured to calculate a risk assessment number based on the sub-population to which the at least one individual belongs and the HIDEN for the most recent RHI event. A risk assessment notification means is communicatively coupled to the computer or to another computer, the risk assessment notification means configured to provide a notification of the risk assessment number.

In one embodiment, the head impact dose equivalent number (HIDEN) process is further weighted by the time to an end of a season or predetermined activity period.

In another embodiment, the notification means further provides each new risk assessment number in about real-time.

In another embodiment, the head impact dose equivalent number (HIDEN) process runs an equation:

$$C - HIM(d)_{TUA} = \sum_{i=1}^{n} \left( \frac{h_{t_{i,d}}}{\max(t_D - t_d, 1)} \right)$$

where a helmet impact measure (HIM) value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed to yield a cumulative HIM value (C-HIM).

In yet another embodiment, the head impact dose equivalent number (HIDEN) process runs an equation:

$$C - HIM(M)_{TUA} = \sum_{d=1}^{M} \left( \sum_{i=1}^{n} \frac{h_{t_{i,d}}}{\max(t_D - t_d, 1)} \right)$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed to yield a cumulative HIM (C-HIM) weighted for the TUA over a total of M days.

In yet another embodiment, the head impact dose equivalent number (HIDEN) process runs an equation:

$$C - HIM(d)_{TBH+TUA} = \sum_{j=0}^{n-1} \left( \left( h_{t_{n-j,d}} + \sum_{i=1}^{n-j-1} h_{t_{n-i,d}} \left( \frac{1}{t_{n-j,d} - t_{n-i,d}} \right) \right) \frac{1}{\max(t_D - t_d, 1)} \right)$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed and cumulative measures are weighted for both the interval of time between hits and the interval of time from hit to post-season assessment include properties from the two individual models, and are described as follows for single day to yield a time between hits and a time until assessment combined (TBH+TUA).

In yet another embodiment, the head impact dose equivalent number (HIDEN) process runs an equation:

$$C-HIM(M)_{TBH+TUA} = \sum_{d=1}^{M}\left[\sum_{j=0}^{n-1}\left(\left(ht_{n-j,d} + \sum_{i=1}^{n-j-1} ht_{n-i,d}\left(\frac{1}{t_{n-j,d}-t_{n-i,d}}\right)\right)\frac{1}{\max(t_D-t_d,1)}\right)\right]$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed and cumulative measures are weighted for both the interval of time between hits to yield a cumulative HIM (C-HIM) weighted for TBH and TUA combined over a total of M days.

In yet another embodiment, the head impact dose equivalent number (HIDEN) process runs an equation:

$$HIDEN_n = ht_n + \sum_{i=1}^{n-1} ht_{n-i}\left[\frac{1}{t_n - t_{n-i}}\right]$$

where, $HIDEN_n$ is the head impact dose equivalent number following a most recent head impact, $ht_n$ is a magnitude of the energy of the most recent head impact, $ht_{n-i}$ is the magnitude of the energy of an n-i previous head impact, n is a total number of RHI, $t_n$ is the time of the most recent head impact, and $t_{n-i}$ is a time between a most recent RHI event n and an $i^{th}$ RHI event In yet another embodiment, the head impact dose equivalent number (HIDEN) process runs an equation:

$$HIDEN_n = ht_n + \sum_{i=1}^{n-1} ht_{n-i}\left[\frac{1}{t_n - t_{n-i}}\right]$$

where, $HIDEN_n$ is the head impact dose equivalent number following the most recent head impact, $ht_n$ is the magnitude of the energy of the most recent head impact, $ht_{n-i}$ is the magnitude of the energy of an n-i previous head impact, n is a total number of RHI, $t_n$ is the time of the most recent head impact, and $t_{n-i}$ is the time between the most recent RHI event n and the $i^{th}$ RHI event.

In yet another embodiment, the head impact dose equivalent number (HIDEN) process runs an equation:

$$HIDEN_n = \sum_{i=1}^{n}\frac{ht_i}{\max(1, t_S - t_i)} + \sum_{i=1}^{n-1}\frac{ht_{n-i}\left[\frac{1}{t_n - t_{n-i}}\right]}{\max(1, t_S - t_{n-i})}$$

where, $HIDEN_n$ is the head impact dose equivalent number following a most recent head impact, now also as a function of time into a playing season (or, equivalent period of time), $ht_i$ is the magnitude of the energy of the most recent head impact, $ht_{n-i}$ is the magnitude of the energy of the n-i previous head impact, n is the total number of RHI this calculation, $t_s$ is the time to the end of the current playing season, and $t_i$ is the time of the most recent head impact.

In yet another embodiment, the sensor system includes at least one accelerometer or at least one gyro.

In yet another embodiment, the sensor system includes at least one camera to provide at least one image of an impact to the individual and wherein the at least one image of an impact is converted or used to estimate to an energy value of an RHI corresponding to the impact.

In yet another embodiment, the computer is communicatively coupled to a non-volatile memory having stored thereon a pre-recorded video footage data from one or more video cameras of the sensor system to estimate an energy of each RHI event.

In yet another embodiment, the system to assess risk includes a wireless sensor system communicatively coupled to the computer.

In yet another embodiment, the system to assess risk is disposed in a head gear including the sensor system, the computer, the clock, and the head impact dose equivalent number (HIDEN) process running on the computer, and the system to assess risk is wirelessly coupled to another computer or display device which displays a most recent HIDEN for each individual.

In yet another embodiment, the sensor system includes at least one sensor disposed in a mouth guard.

In yet another embodiment, the sensor system includes at least one sensor disposed in a skin patch or a sub-dermal implant.

In yet another embodiment, the sensor system includes at least one sensor disposed in a dental filling or dental implant.

In yet another embodiment, the sensor system includes at least one sensor disposed in an ear insert.

In yet another embodiment, the sensor system includes at least one sensor disposed in an ocular device.

In yet another embodiment, the ocular device includes at least one sensor disposed in a contact lens or eye glasses.

In yet another embodiment, the sensor system includes at least one sensor worn on the at least one individual's body other than as part of a head gear.

In yet another embodiment, the head gear includes a helmet or a skull cap.

According to another aspect, a method to assess risk of changes to brain white matter based on a head impact dose equivalent number includes: providing a sensor system adapted to directly or indirectly measure an energy of each impact to at least one individual that causes a repetitive head impact (RHI), the at least one individual belonging to a sub-population, a clock means configured to provide a time, and at least one computer communicatively coupled to the sensor system or to a non-volatile memory having stored thereon data from, and communicatively coupled to the clock means, and a notification means communicatively coupled to the at least one computer; estimating a directly or indirectly measure an energy of each impact to at least one individual that causes a repetitive head impact (RHI), the at least one individual belonging to a sub-population; calculating a head impact dose equivalent number (HIDEN) process running on the computer, the HIDEN process to calculate a HIDEN for a most recent RHI event based on an energy of the most recent RHI event, a time of the most recent RHI, and all previously recorded RHI events available in a non-volatile memory, each RHI event of all previously recorded RHI events time weighted by the time between each of the all previously recorded RHI events and the time of the most recent RHI; calculating a risk assessment number using a sub-population function based on the sub-population to which the at least one individual belongs and the HIDEN for the most recent RHI event; and notifying at least one other individual by use of the notification means of the risk assessment number.

In one embodiment, the step of calculating a HIDEN is further weighted by the time to an end of a season or predetermined activity period.

In another embodiment, the step of calculating a HIDEN comprises calculating a HIDEN based an equation:

$$HIDEN_n = ht_n + \sum_{i=1}^{n-1} ht_{n-i} \left[ \frac{1}{t_n - t_{n-i}} \right]$$

where, $HIDEN_n$ is the head impact dose equivalent number following the most recent head impact, $ht_n$ is the magnitude of the energy of the most recent head impact, $ht_{n-i}$ is the magnitude of the energy of an n–i previous head impact, n is a total number of RHI, $t_n$ is the time of the most recent head impact, and $t_{n-i}$ is the time between the most recent RHI event n and the $i^{th}$ RHI event.

In yet another embodiment, the step of calculating a HIDEN comprises calculating a HIDEN based an equation:

$$HIDEN_n = \sum_{i=1}^{n} \frac{ht_i}{\max(1, t_S - t_i)} + \sum_{i=1}^{n-1} \frac{ht_{n-i} \left[ \frac{1}{t_n - t_{n-i}} \right]}{\max(1, t_S - t_{n-i})}$$

where, $HIDEN_n$ is the head impact dose equivalent number following a most recent head impact, now also as a function of time into a playing season (or, equivalent period of time), $ht_i$ is the magnitude of the energy of the most recent head impact, $ht_{n-i}$ is the magnitude of the energy of the n–i previous head impact, n is the total number of RHI this calculation, $t_S$ is the time to the end of the current playing season, and $t_i$ is the time of the most recent head impact.

According to yet another aspect, a method to define a sub-population function to convert a HIDEN to a risk assessment value includes: providing a plurality of individuals of a sub-population type outfitted with a sensor system to directly or indirectly measure RHI caused by impacts to each individual of the plurality of individuals and a system to observe brain white matter changes or brain white matter injury; acquiring HIDEN data for each individual of the plurality of individuals over a period of time; acquiring brain white matter changes or brain white matter injury for each individual of the plurality of individuals at intervals over the period of time; and correlating the brain white matter changes or brain white matter injury for each individual of the plurality of individuals to the HIDEN data to develop the sub-population function.

In one embodiment, the system to observe brain white matter changes or brain white matter injury includes a diffusion tensor imaging (DTI) system.

The foregoing and other aspects, features, and advantages of the application will become more apparent from the following description and from the claims.

BRIEF DESCRIPTION OF THE DRAWINGS

The features of the application can be better understood with reference to the drawings described below, and the claims. The drawings are not necessarily to scale, emphasis instead generally being placed upon illustrating the principles described herein. In the drawings, like numerals are used to indicate like parts throughout the various views.

FIG. 7A shows an image of WM structures (left), and significant DTI changes from Time 1 to Time 2 (right) in a football player;

FIG. 7B shows an image of WM structures (left), and significant DTI changes from Time 1 to Time 2 (right) in a control subject;

FIG. 10 shows table 1;

FIG. 11 shows table 2;

FIG. 12 shows two exemplary HIDEN calculations for a hypothetical player;

FIG. 16 shows a table of mean (range) helmet impact metrics for 10 athlete subjects;

DETAILED DESCRIPTION

Figure 1:
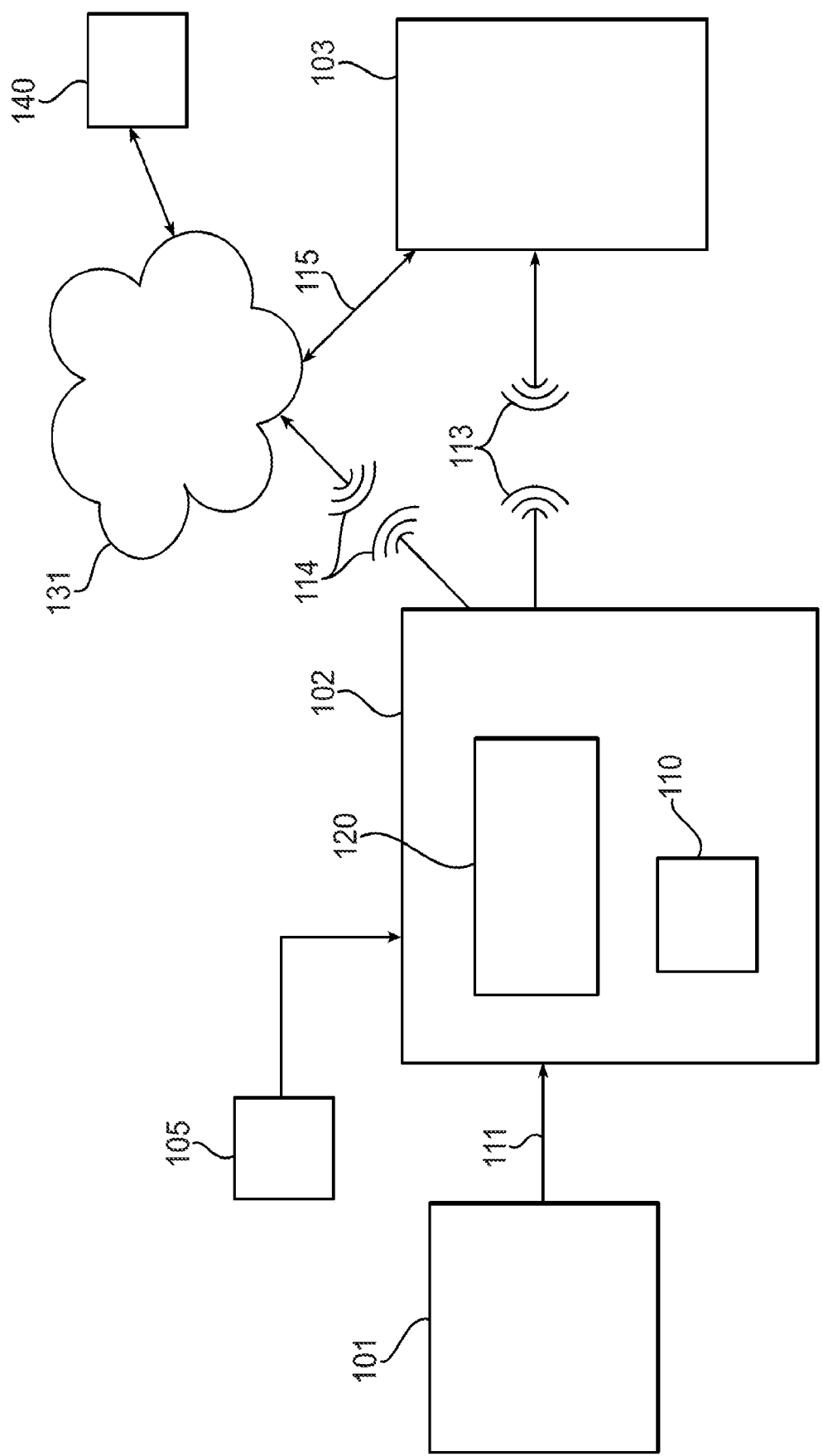
FIG. 1 shows a simplified block diagram of exemplary hardware suitable for use to mitigate changes to brain white matter based on a head impact dose equivalent number (HIDEN)

DEFINITIONS: Repetitive head impact (RHI)—RHI includes an impact to any part of a human body which imparts g-forces to brain white matter in the head. Impacts to the head are included and the most common source of an RHI event. However, it is also common for an impact to another part of the body, such as for example a shoulder to shoulder impact in a contact sports activity to cause an RHI event of the human brain as mechanical forces are translated from the shoulders through the musculoskeletal system to the head.

Concussion: The clinical definition of concussion is characterized by immediate and transient alteration in brain function, including alteration of mental status and level of consciousness, resulting from mechanical force or trauma. Occurrence of a concussion can be assigned by a trained medical professional based on observation of an event or more likely based of symptomatic behaviors (e.g. confusion, memory loss, etc.). As concussion has entered the mainstream conversation, a concussion is also now commonly declared by non-medically trained coaches, teachers, and parents. Concussion is a diagnosis of a brain injury cause by a mechanical force or trauma. As such, concussion is a positive indication of brain injury after the event. There is no accepted definition that says concussion is associated with a structural change in the brain. However, a concussion is typically associated with temporary functional disruption. The relationship between concussion and structural brain injury is weak; there are many people that have had a concussion without brain injury (as indicated by DTI), as well as many who sustain hits (without a concussion) who do show structural brain injury on DTI.

Clock means: RHI data can be time stamped by any suitable clock means. Typically, a clock can be provided by a hardware clock chip with a clock provided by any suitable oscillator (e.g. a crystal oscillator) or resonator. The clock means can also be provided, for example, by a software process running on any suitable processor. The clock means can also be provided by any available external clock, such as for example, from a global positioning system (GPS) receiver, or from any suitable network connection, such as for example a network connection to the Internet. The clock means could be an arbitrary unit (e.g. processor cycles) as long as it can later be converted to a time stamp, or at least be able to be used to determine the time between RHI events.

Sensor system: A sensor system includes one or more accelerometers and/or one or more gyros. Sensors such as accelerometers and/or gyros can be worn in headgear, such as, for example, a helmet or skull cap. A sensor system can also include remote sensing of impacts to the body which result in RHI, such as, for example a system of one or more imaging devices (e.g. one or more video cameras). Individuals being monitored can optionally wear optical or electronic markers on their body or on their clothing to help convert images or other remotely sensed data to impacts and/or RHI events and to estimate the energy of each of the RHI events. It is contemplated that such remote sensing systems can also be based on radar (radio based range and motion sensing) or lidar (laser or other optical based range and motion sensing). Processing can be in real-time, near real-time, and/or post processing of previously recorded data (e.g. post processing for risk assessment using previously recorded video footage, or previously recorded sensor data). One or more sensors can be disposed in a mouth guard, skin patch or a sub-dermal implant, a dental filling or dental implant an ear insert, an ocular device, such as contact lens or eye glasses (e.g. Google Glass™), worn on an individual's body other than as part of a head gear, or worn in or on head gear such as a helmet or a skull cap.

Risk assessment notification means: A risk assessment notification means includes any suitable notification such as, for example, a risk assessment value displayed on a computer display, a smart phone application, a display on another computer (including, for example, a dedicated processor based computer display, a personal computer, laptop computer, a notebook computer, a netbook computer, tablet computer, etc.). A risk assessment notification means also includes a text message, an instant message, an automated phone call (voice or text), or an email. A risk assessment notification means can include a light or other visual or audio indication when a risk assessment value exceeds a predetermined risk assessment value threshold.

Head impact dose equivalent number (HIDEN) process: A HIDEN process calculates a HIDEN for a most recent RHI event based on the energy of the most recent RHI event, a time of said most recent RHI, and all previously recorded RHI events. Each RHI event of all previously recorded RHI events time is weighted by the time between each of said all previously recorded RHI events and said time of said most recent RHI.

Sub-population function process: A sub-population function process includes a function which converts a HIDEN to a risk of brain white matter change or brain white matter injury. A sub-population function can be developed or derived from a clinical study of that sub-population. For example, HIDEN data (e.g. from helmet mounted sensors) and a diffusion tensor imaging (DTI) study can be used to generate a standard receiver operating characteristic (ROC) curve from which a sub-population function can be derived by regression or curve fitting. While typically including a non-linear operator (e.g. including an exponential operator), a sub-population function can have any suitable mathematical form including any suitable linear or non-linear relationship or equation.

Evidentiary data: The evidentiary data discussed herein was obtained during about a six month study of division III collegiate football players. While the techniques of study described herein are believed applicable to professional football players (e.g. NFL™ players), we have not yet performed clinical studies of professional athletes.

As described hereinabove, in recent years there has been increasing awareness in the medical community, as well as in the general public, of long term or chronic effects resulting from RHI. There have been two separate but ever-converging tracks of research. Military research in head trauma results largely from the unfortunate consequences of asymmetric warfare and the corresponding widespread use of improvised explosive devices (IED) that makes head trauma and brain injury all too common now among combatants. Another rapidly emerging area of study relates to brain trauma from participation in sports activities. Beginning with an awareness of chronic brain injury to boxers, this field of research quickly has extended to U.S. professional football and the national football league (NFL™) and now to college and high school sports activities as well.

Combined with the new national push for more brain research, these seemingly disparate areas of head injury are combining into studies and searches for better understanding of how to study brain injury and its chronic after-effects. Much of the focus on head injury and traumatic brain injury has focused heretofore on concussions.

A concussion results when a head impact imparts enough mechanical energy to the head to jar the brain enough a temporary change in mental status (e.g. loss of consciousness, amnesia, or confusion). A concussion is often, but not necessarily, associated with evidence of structure brain injury. With good reason, the medical, sports, and military communities typically track concussive events and their after-effects. However, we believe that the concussion centric focus of the prior art is misdirected and problematic.

We previously described a new method for determining whether a subject has suffered a mild traumatic brain injury in U.S. Patent Application Publication No. 20120244555 A1. The method comprises selecting a subject exposed to a head trauma; and determining whether a body fluid sample obtained from the selected subject comprises smaller than normal high density lipoprotein (HDL) particles, larger than normal HDL particles, or both; wherein detection of the smaller than normal HDL particles, larger than normal HDL particles, or both, indicates that the subject has suffered a mild traumatic brain injury. The '555 patent publication is incorporated herein by reference in its entirety for all purposes. The techniques of the '555 patent publication relate to biochemical analysis, and pending further advances in wearable real-time and near real-time biochemical analysis, might still be less convenient or too costly for field use.

Protective head gear, such as, for example, military and sports helmets, have been outfitted with one or more sensors, such as one or more accelerometers and/or one or more gyros to register severe hits to the head. The common wisdom related to a threshold for head impact or injury of medical significance and concern regarding exiting an activity such as a sports activity has been a concussion event or suspicion or high likelihood of a concussive event. Therefore, generally such instrumentation and monitoring efforts have been directed towards detection of a concussive event.

Relatively recently, in Persistent, Long-term Cerebral White Matter Changes after Sports-Related Repetitive Head Impacts, J. Bazarian, et. al., PLOS ONE, published Apr. 16, 2014, which it attached hereto as Appendix A, based on 6 months of evidence, which is considered chronic in public health, we came to the startling realization that chronic injury onset can and does occur at impact energies accumulated over the course of a collegiate football season far lower than the energy levels of head impact associated with a concussion. We performed the study to characterize the magnitude and persistence of RHI-induced white matter (WM) changes, to determine their relationship to kinematic measures of RHI, and to explore their clinical relevance.

We conducted an observational study of 10 Division III college football players and 5 non-athlete controls during the 2011-12 playing season. All subjects underwent diffusion tensor imaging (DTI), physiologic, cognitive, and balance testing at pre-season (Time 1), post-season (Time 2), and after 6-months of no-contact rest (Time 3). Head impact measures were recorded using helmet-mounted accelerometers. The percentage of whole-brain WM voxels with significant changes in fractional anisotropy (FA) and mean diffusivity (MD) from Time 1 to 2, and Time 1 to 3 was determined for each subject and correlated to head impacts and clinical measures.

Our results included determination of the total head impacts for the season for each individual athlete that ranged from 431-1,850. No athlete suffered a clinically evident concussion. Compared to controls, athletes experienced greater changes in FA and MD from Time 1 to 2 as well as Time 1 to 3; most differences at Time 2 persisted to Time 3. Among athletes, the percentage of voxels with decreased FA from Time 1 to 2 was positively correlated with several helmet impact measures. The persistence of WM changes from Time 1 to 3 was also associated with changes in serum ApoA1 and S100B autoantibodies. However, WM changes were not consistently associated with cognition or balance, nor were WM changes detectable by routine observation.

We concluded that a single football season of RHIs without clinically-evident concussion resulted in WM changes that correlated with multiple helmet impact measures and persisted following 6 months of no-contact rest. This lack of WM recovery can contribute to cumulative WM changes with subsequent RHI exposures.

We have determined that injury to the white matter of the brain related to RHI over a period of time can occur at levels far below the head impact energy level of a concussive event. Moreover, relatively low level impacts can lead to chronic injury, even where there has never been a concussive event. We realized that the severity of cumulative white matter brain injury caused by repetitive head impacts (RHI) is directly related to the time between successive impacts, or more specifically, the time of each of the previous RHI events with respect to the time of the most recent RHI event. We found that we could predict with surprising accuracy the cumulative effect of RHI by a combination of considering the magnitude of the energy of each individual head impact with a time weighted factor of the time since the previous head impact. The correlation of white matter brain changes to cumulative head hits provides the basis for the new system and method of risk mitigation provided herein, both to assess and to prevent white matter injury based on the time between RHI and the energy of each recorded RHI.

RHI (incurred during sports, military duty, and alike) produce changes in brain white matter (WM) that can contribute to the development or progression of chronic traumatic encephalopathy (CTE) at later time points. There is a relationship between acute brain white matter changes and the total number and magnitude of RHIs over a season of play. Prior research has not recognized the correlation between the interval of time between impact exposures (TBE) or the period of time between an impact and the outcome measure (e.g., diffusion tensor imaging). The frequency of exposures or time between RHIs influences brain short term or long term white matter changes which may or may not resolve and that might be related to chronic conditions and/or early onset of later life neurodegeneration including brain disease, such as, for example, early-onset Alzheimer's disease and chronic traumatic encephalopathy (CTE).

Concussions are a frequent occurrence among athletes involved in contact sports such as football, ice hockey, soccer, and lacrosse (1.6-3.8 million/year). However, sub-concussive repetitive head impacts (RHI) are even more common. As described hereinabove, RHI causes structural alterations in the neuronal axon and microenvironment in the brain white matter. In the short term RHI increase the risk for neurocognitive symptoms such as memory and planning deficits, poor verbal and visual memory and impaired conceptual thinking, reaction time and concentration. In the long term, RHI may increase the risk for developing neurodegenerative diseases such as AD, chronic traumatic encephalopathy (CTE) and early-onset dementia.

In recent years, there has been significant awareness of the danger of concussions. There has also been some measurement of the energy level of an individual impact event computed with regard to the time duration of the impact event itself (e.g., head injury criterion as used by the National Highway Traffic Safety Administration (NHTSA)). Most of the current systems and methods related to head impact are concussion centric. For both legal liability reasons and medical reasons, most if not all such systems caution users to observe persons being monitored for by their sensors for signs of concussion. Many rely on the Centers for Disease control and prevention (CDC) guidelines for diagnosing a possible concussion. For example, one CDC online publication forms categories of concussion symptoms including thinking, remembering, physical, emotional, mood, and sleep. The common wisdom of today is to monitor at risk individuals by head impact sensors where possible, and observe all persons for symptoms of concussion, and then to seek medical assistance.

In other words, it is commonly believed that short of a concussion, other head impacts are relatively safe, or at least nothing more than a relatively minor injury to be associated with the normal aches and pains of daily living. Our research indicates to the contrary, that RHI causes white matter changes at relatively low level head impacts (e.g., by about at least 10 g impacts) and that depending on the time between successive low level impacts, the energy of the successive impacts, white matter changes may persist, despite prolonged rest, potentially contributing to chronic brain injury (long term or permanent brain injury).

Seemingly "invisible" threats to human health are well known in the medical field. For example, gas or chemical detection equipment is needed to assess a threat from low level toxic chemical or gas exposure threats (e.g., CO detectors in the home). Another example of an invisible health threat is radiation exposure. Radiology professionals, such as radiology and nuclear medicine technicians are required to wear a radiation dosimeter, such as an electronic dosimeter or a film badge when working to track cumulative dose caused by invisible ionizing radiation. White matter brain changes and white matter brain injuries that we recently identified at relatively low levels of RHI were heretofore, largely unknown.

One similarity that RHI has with smoking cigarettes, another behavior with well-known health risks, is that it took many years before the medical community realized the dangers of long-term smoking, even at relatively low levels. Also, the corollary question, "How many cigarettes are safe?", does not directly apply to the problems of head impact. However, another similarity of smoking to RHI is that, there was a time where smoking in moderation was believed to be relatively safe. The common wisdom is that low level RHI are relatively safe.

Particularly with regard to young adult participation in contact sports, the current head concussion centric head impact safety criterion is insufficient. Waiting until early onset dementia or CTE has occurred to take action is too late. There is a need for a head impact monitoring system that can record and time stamp each RHI to consider the effects of the time duration between such events, including RHI well below the energy of an impact which causes brain white matter damage.

The system and method provided herein calculates repetitive head impact dose equivalent numbers (HIDENs) based on the time between head impacts and the energy of each impact. Our new HIDEN based system provides a dose equivalent number which allows for a quantitative measurement and action based on risk assessment of white matter changes and white matter injury to the brain.

Various embodiments of the system and method calculate each individual's present total magnitude of cumulative time weighted head impacts, i.e., previous recorded RHI weighted by impact energy and time between impacts in real-time or near real-time (about real-time). The new index of RHI weighted by impact energy and time between impacts is referred to as a head impact dose equivalent number (HIDEN). HIDEN is calculated from the energy of each RHI and the time between each of the previously recorded RHI events, or more specifically the time between each of the previous RHI events and the time of the more recent RHI event.

Prior art systems and methods identify severe head impacts to warn that a concussion has occurred. The primary concern is that the neurological effects of repetitive, sub-concussive head hits that occur gradually and over many year will not go unnoticed and not be recognized until permanent, irreversible damage has occurred (e.g. cognitive decline, dementia, CTE, etc.). However, once symptoms of dementia are observed, the threat of long term or chronic brain injury, or accelerated brain degeneration in later life is likely. While the analogy to smoking as note hereinabove is imperfect, waiting until the symptoms of cognitive decline or dementia are observable is analogous to waiting until a suspicion or diagnosis of lung cancer to stop smoking.

The system and method described herein based on HIDEN process provides a way to asses risk of white matter injury before permanent, irreversible damage has occurred. Following each RHI, an indicia of probable risk sufficient to mitigate a far more serious and permanent injury can be determined and acted upon.

One difference and technological advance of the HIDEN based system is that another entire level of previously unknown criteria now calculated by the HIDEN process provide an assessment of an otherwise previously "invisible" risk of brain damage. This new criteria are weighted by both the energy of each individual impact, plus the time since the last recorded HIDEN value, and all previously recorded HIDEN values for a duration of time, weighted with reference to the time of the most recent RHI event.

FIG. 1 shows a block diagram of a simplified hardware configuration of a system 100 for measuring and recording HIDEN from RHI for at least one individual. At least one sensor of a sensor system 101 detects each RHI. In many embodiments, the at least one sensor 101 is literally worn by each individual on or near the individual's head. For example, the at least one sensor 101 can be mounted inside a helmet of the type associated with any particular activity. Alternatively, we contemplate that at least one sensor 101 can be located in a jaw protection device worn by an individual. Also, as described hereinbelow in more detail, we contemplate that RHI can be measured by remote sensing, such as, for example, by at least one camera viewing a playing field. In the case of remote sensing, as by at least one camera, there might be markers on each player, such as for example, recognizable points on the individual player's outer wear, however individuals need not wear active RHI accelerometer or gyroscopic sensors. A clock means 105 provides a time to a computer 102 so that incoming data from sensor system 101 can be time stamped. There can be determination of a RHI event by threshold of energy being exceeded as determined by at least one sensor of sensor system 101. The time at which the energy threshold was exceeded can be recorded and coupled by any suitable data base and/or data structure to the record of the magnitude of the energy of that particular event. A computer 102 is communicatively coupled to sensor system 101 and to clock means 105 to receive the magnitude of the energy of each RHI event and the time and to associate thereto a RHI time stamp and to record a time stamped energy for each RHI event, typically to a non-volatile memory 110. A head impact dose equivalent number (HIDEN) process 120 typically runs on computer 102. HIDEN process 120 calculates a HIDEN for each RHI event based on the time stamped energy magnitude of a most recent RHI event, the time between the most recent RHI event and a most recent previous RHI event, and all previously recorded HIDEN events stored for a duration of time in a non-volatile memory, such as, for example, non-volatile memory 110.

A notification component 103 is communicatively coupled to computer 102. The notification component makes the most recent risk of changes to brain white matter based on HIDEN available for monitoring an individual's risk of brain white matter change or injury resulting from repetitive head impact (RHI) in about real-time.

An individual could be removed from an activity following a most recent risk assessment output caused by the most recent RHI event after a notification by the notification component that their HIDEN exceeds a pre-determined risk threshold. In some embodiments, the notification component 103 could be as simple as a bright light worn on a helmet. However, more typically, there will be a wireless link between at least a first part of the apparatus and a second part of the apparatus, where there can be any suitable alpha-numeric and/or graphic display showing the risk assessment for at least one individual.

As described in more detail hereinbelow, risk assessment can be reported using any suitable scale ranging, for example, from a unit-less number to a percentage.

For example, in some embodiments, communication path 111 from sensor system 101 might be a wireless communications link used to convey raw sensor system 101 information to computer 102 located at another location, typically at a central monitoring location.

More typically, computer 102 and clock means 105 can be disposed physically close to the sensor system (where the sensor system comprises at least one accelerometer and/or gyro), such as in a helmet, where communication path 111 can be hardwired and/or use a local short range wireless link, such as, for example Bluetooth™. In such embodiments, raw time-stamped RHI events and/or HIDEN and/or risk assessment data following each RHI event can be sent to another computer via any suitable wireless means 113. The wireless means can be a radio frequency means of data communications and may or may not further make use of any suitable computer network. For example, a helmet mounted computer system 102 can communicate wirelessly 114 (e.g., WIFI) to a network 131 with at least one monitoring computer receiving raw time-stamped RHI events and/or HIDEN and/or risk assessment data via the network 131.

In some embodiments, the network can be the Internet, and/or a local network connectively coupled to the Internet. Display means 103, which is usually separate from computer 102, typically comprises at least one computer processor. In some embodiments, display means 103 might be a laptop computer, notebook computer, tablet, or any other suitable computer connected to the network 131 by any suitable wired or wireless means 115 (e.g., WiFi) with its own display screen. In other embodiments, there can be a two or more display means 103, where each of the remote computer based devices (e.g., a computer, laptop, notebook, netbook, tablet, smart phone, etc.) can receive raw time-stamped RHI events and/or HIDEN data for at least one individual directly from at least one computer 102 in the field (e.g., in player helmets). In other embodiments, the display means 103 can also make raw time-stamped RHI events and/or HIDEN and/or risk assessment data and/or further processed data based on raw time-stamped RHI events and/or HIDEN and/or risk assessment data, for at least one individual available to any other suitable digital devices via network 131.

In some embodiments, as described hereinabove, previous raw time-stamped RHI events and/or HIDEN and/or risk assessment data are typically stored locally on a non-volatile memory 110 for a period of time. In other embodiments, there can be previous raw time-stamped RHI events and/or HIDEN and/or risk assessment data stored on the device of the display means 103, or on another computer accessible via network 131, or on a remote non-volatile memory 140, such as, for example can be accessible via a server as cloud storage. Where there is additional non-volatile memory having stored thereon raw time-stamped RHI events and/or HIDEN and/or risk assessment data for at least one individual, the remotely stored data could be stored for a longer period of time than the time period of data retention on memory 110, typically in close proximity (e.g., on the same circuit board) to computer 102. For example, local memory 110 can have raw time-stamped RHI events and/or HIDEN and/or risk assessment data from a particular playing season or a particular game, while remote memory 140 can include raw time-stamped RHI events and/or HIDEN and/or risk assessment data for an individual's lifetime, or for a season, or for the duration of a high school and/or college athletic period, or for the duration of a professional sports career, etc. New systems and methods as we describe herein will undoubtedly become more accurate predictors of brain injury risk as more data are collected.

In some embodiments, there might be national and/or international cooperation to share raw time-stamped RHI events and/or HIDEN and/or risk assessment data from many individuals to improve our understanding of human brain health and brain injury prevention. In such instances of sharing, a remote memory 140, or any other suitable remote storage or database, such as can be in the cloud can be made available to brain researchers, safety professionals, and/or national or international health organizations. Such availability can follow any suitable athletic or medical protocol for sharing human data and may or may not be available as anonymous data or semi-collated data (e.g., summary HIDEN data for anonymous college football players by playing season and by college).

The new system and method to predict risk of changes to brain white matter caused by RHI events can report each individual's risk assessment and/or HIDEN and/or can provide an alarm when any individual's risk assessment exceeds a predetermined threshold. When possible or practical, an individual can stop or cease activities when their risk assessment exceeds their predetermined threshold. Especially for the case of more frequently occurring low level RHI, an individual risk assessment will exceed their predetermined risk assessment threshold long before any observable brain injury.

Various embodiments use a variety of different sensor means ranging from at least one accelerometer and/or at least one gyro, such as the helmet mounted sensors used for concussion detection to remote sensing of head impacts by various optical means including, for example, at least one camera view of a playing field.

Another reason for a wide variety of embodiments is the economic cost of implementation. It is contemplated that well-funded organizations such as the military or professional sports teams, and even some college level teams can purchase relatively sophisticated monitoring and computing systems with less concern for cost. Far lower cost embodiments are also contemplated. For example, as parents become aware of the relatively low threshold for chronic white matter brain injury with possibly long term negative brain health consequences, brain injury risk mitigation based on HIDEN can be adopted by high school sports activities and possibly eventually elementary schools as well.

Individual Risk Assessment Thresholds: In some embodiments, risk assessment thresholds (an individual's threshold for white matter injury) can be determined with a relatively high level of confidence for each monitored individual. However, individual assessment, when based, for example, on advanced medical diagnostic tools, such as for example, diffusion tensor imaging (DTI), a common tool in our research, is likely to have a relatively high cost of implementation. Such medically advanced testing for a professional athlete, such as, for example, a professional football player, is possibly practical. It is contemplated that by preliminary impact measurements combined with DTI, risk assessment values and/or risk assessment thresholds tailored to individual players can lead to relatively accurate results and white matter brain injury mitigation, such as by determining in real-time or near real-time when a player needs to exit the game to avoid a high likelihood of white matter brain injury.

Generalized risk assessment values or risk assessment thresholds (non-specific to a particular individual): We contemplate that future testing can yield such risk assessment values or risk assessment thresholds for teenage and possibly pre-teenage children. Based on our preliminary studies, it is likely that there will be variation between individuals of the HIDEN which causes white matter brain injury onset or actual white matter injury. In one cost-effective embodiment, the projected average values of risk assessment values or risk assessment thresholds can be used, for example, as can be determined and/or estimated by sex and age. Risk assessment values or risk assessment thresholds can be optionally further adjusted by other easily ascertained individual factors, possibly factors such as, for example, body mass, body size, body shape, genetics, etc.

Wearable Impact Sensors and Sensor Packages: Wearable impact sensors and sensor packages are well known in the art, particularly related to the understanding of the prior art, that it was important to monitor for concussions. There is a diverse selection of sensor systems commercially available. These systems can be generally categorized into two groups: Group I Sensors are sensors that collect and provide limited data; usually the number of hits sustained and some include the force of the hit (in g-force values). These sensors do not provide more descriptive characteristics of each hit. Group II Sensors are descriptive sensor systems that provide not only the number of hits, but biomechanical characteristics of the hit such as linear and rotational acceleration of each hit, duration, and head location of each hit.

Exemplary Group I Sensors Include: Impakt Protective Inc. of Kanata, Ontario, CA offers The Shockbox helmet Sensor which is designed to be attached to the top of a hockey, football, snow sports, lacrosse, equestrian or bike helmets and provides an indication of a head impact that could result in a concussion. Shockbox helmet sensors can warn parents, athletic trainers and coaches when a player impact should be assessed for concussion.

Archetype Corp. of Birmingham, Ala. offers the PlayerMD Biometric Headgear including sensors on skullcaps and head bands.

The Impact Indicator available from Battle Sports Science, LLC of Omaha, Nebr. measures the force and duration of a hit to a player's helmet and lights a light. IMPACT INDICATOR chin strap uses micro sensor and software to measure and calculate the force and duration of a hit to a player's helmet. IMPACT INDICATOR measures head impacts according to the Head Injury Criterion (HIC). The Impact Indicator does not react to every hit to the head, only those hits to the head that measure at the Wayne State Head Injury Criterion (HIC) levels. Concussion can occur at or below those levels.

The Reebok Checklight, available from mc10, Inc. of Cambridge, Mass. uses multiple sensors capture head impact data during play tucked under any helmet as a skullcap. It senses when the wearer has been dealt a major blow to the head with a yellow light to signal a moderate impact and red light to indicate a severe impact. The mc20 website features CDC criterion for concussion recognition ranging from what is a concussion to signs and symptoms of a concussion and what to do if a concussion is suspected.

Brain Sentry of Bethesda, Md. offers a helmet-mounted sensor which records the number of hits sensed over a day, a week, and a year. A red LED helps to identify the "big hits".

SafeBrain of Calgary, AB, CA offers a helmet sensor that measures G-force impact, and if a player is hit hard enough, with a force of any specific hit that exceeds their personal threshold, then a flashing light on the sensor will alert trainers that the athlete needs to be evaluated for a head injury. The sensors only begin to log data above threshold value. The emphasis on concussion detection and recognition and second impacts after a major impact.

Group II Sensors Include: Riddell of Rosemont, Ill. offers helmets with sensors that measure the magnitude, location, and direction of a hit. The collected data can then be uploaded to a user's computer and analyzed with a Web-based application. Riddell's Revolution IQ Hits helmets include six accelerometers built into its liner that measure the acceleration of the player's head, not the helmet. The accelerometers are available from Analog Devices of Norwood, Mass. Similar sensors available to the auto industry are used in automotive airbags. The sensors measure both the linear and rotational acceleration of the head, and the resulting reaction force is expressed in g-force. A central server interprets the data, calculating the magnitude of the hit and the location on the head using an algorithm developed by Simbex. The results are visually and numerically displayed to the user; data include the duration and time that the hit took place. Various aspects of the Riddell system have been described in the patent literature, including U.S. Pat. Nos. 6,826,509 B2, 6,826,509 B2, 8,797,165 B2, and U.S. Patent Application Publication No. 2014/0039355. All of the aforementioned Riddell patents and patent application publications are incorporated herein by reference in their entirety as exemplary sensor systems which may be suitable for use in our system and method to detect and mitigate white matter brain changes and white matter brain injury.

Gforcetracker Inc. of Markham, ON, CA offers the GForce tracker an electronic device which is fastened to the inside of a player's helmet. The GForce tracker collects the force, location and frequency of impacts to the head. The software converts data in real-time for player and team analysis. Accurately measures the severity of impacts by converting data such as HIC, GSI, and other formulas into usable reports.

X2 Biosystems of Seattle, Wash. offers the X-Patch having 6 axis impact acceleration sensor modules. Data can be transmitted to an X2 access point located at the sideline and recorded in a cloud database. Access to the player information is subsequently provided to mobile devices at the field of play or anywhere in the world.

i1 Biometrics of Kirkland, Wash. offers the i1 Biometrics Impact Intelligence System which gives sideline personnel the ability to accurately measure the location and level of any given impact, and to establish an athlete's history of exposure and injury.

Triax Technologies Inc of Norwalk, Conn. offers a headband or skullcap which can be worn underneath helmets. The SIM-P provides alerts of head impacts and flags the most forceful, which warrant removal from a practice or game.

From the industry survey hereinabove, it can be seen that the common wisdom of those skilled in the art teaches that head impact sensors need to detect and indicate head impacts with sufficient energy to cause a concussion or traumatic brain injury (TBI). The common wisdom is that users of such devices and other observers should also be on the lookout for observable symptoms of concussions with or without a head impact alarm indication. Unfortunately, to date, those skilled in the art of head impacts have not realized that white matter changes and white matter injuries very likely occur routinely in the human brain at levels well below the accepted wisdom of indexes such as the HIC, TBI, concussion, and highly energetic sub-concussive impacts.

The above group 1 and group 2 systems and methods all lack a quantitative analysis feature for considering a far wider dynamic range of RHI energy levels and the time between such RHI, which are now known or expected to cause white matter brain changes or injury. However, many such systems with hardware and/or firmware or software modification capabilities may be able provide input data suitable to calculate the new HIDEN. To calculate HIDEN, a system will have a means to time stamp RHI events and to record the energy of each RHI event, including those below highly energetic sub-concussive events and well below concussive events. Suitable systems should also have a means to report the HIDEN for each individual in real-time and/or near real-time.

Time Stamp: As described hereinabove, HIDEN is a dose equivalent value determined from the magnitude of two or more RHI events and the time between successive RHI events, or more specifically, the time between each of the previous RHI events and the most recent RHI event. Because HIDEN is based on both a magnitude of each RHI as well as the time between successive RHI, a time of each RHI is recorded (i.e., RHI data for each RHI for each individual player is time stamped). It is unimportant whether the RHI data are measured and time stamped before being transmitted or conveyed by any suitable means from the individual to a processor 102, or if the data are sent to the processor 102 without a time stamp where the time stamp is added on arrival at the processor 102.

RHI Magnitude Data: There can be a plurality of data types for each RHI, such as data from at least one accelerometer and/or at least one gyro, or the data can be combined by any suitable electronic means and/or processor means worn by the individual and transmitted or conveyed by any suitable means from the individual to a processor 102 as a single RHI magnitude value. In other embodiments, there could also be streaming data from the at least one sensor 101, where an RHI event is determined and time stamped by the processor 102.

In one embodiment, a head impact dose equivalent number (HIDEN) process runs the equation:

$$HIDEN_n = ht_n + \sum_{i=1}^{n-1} ht_{n-i}\left[\frac{1}{t_n - t_{n-i}}\right]$$

EQ. 1, where, $HIDEN_n$ is the head impact dose equivalent number following the most recent head impact, $ht_n$ is the magnitude of the energy of the most recent head impact, $ht_{n-i}$ is the magnitude of the energy of the n−i previous head impact, n is the total number of RHI, $t_n$ is the time of the most recent head impact, and $t_{n-i}$ is the time between the most recent RHI event n and the $i^{th}$ RHI event.

Figure 3:
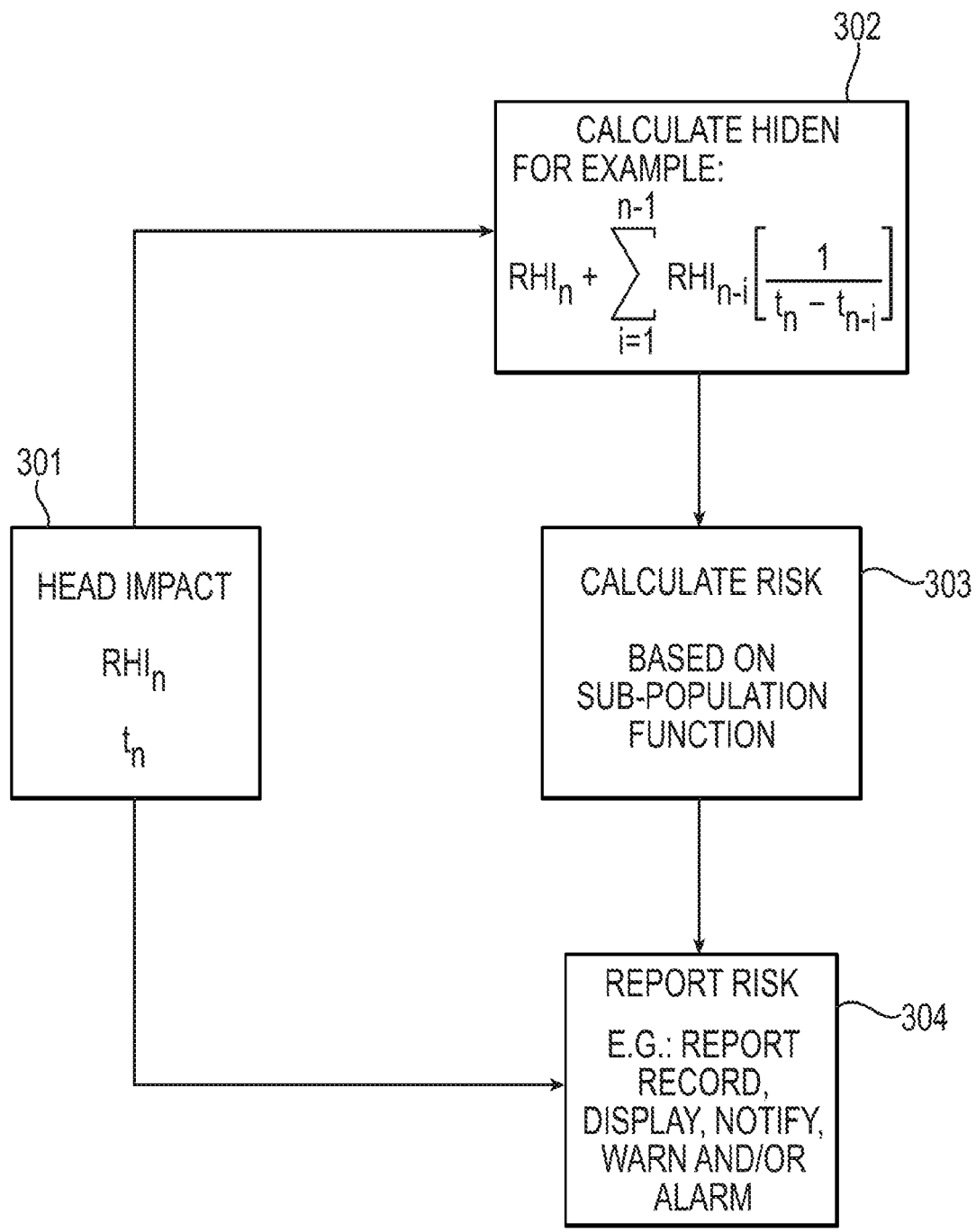
FIG. 3 shows a flow chart of an exemplary process suitable to assess the risk of changes to brain white matter based on head impact dose equivalent number.

FIG. 3 shows a flow chart of an exemplary process suitable to determine HIDENs, risk based on a sub-population function, and to report risk (risk assessment). At head impact 301, a magnitude of the head impact $RHI_n$ and time of the head impact $t_n$ is recorded and provided to the HIDEN calculation 302 and can also be saved to non-volatile memory. HIDEN calculation 302 calculates or retrieves the sum:

$$\sum_{i=1}^{n-1} ht_{n-i}\left[\frac{1}{t_n - t_{n-i}}\right]$$

and calculates a new HIDEN based on the most recent head impact recorded at head impact 301 which can be saved to non-volatile memory. At calculation 303, a risk (risk assessment) is calculated based on a sub-population function. Sub-population functions are described in more detail hereinbelow. At report step 304, the risk assessment calculated at calculation 303 is reported out, such as, for example, by a displayed number, a recorded number, any suitable notification system (e.g. cell phone call, text message, email, risk number in a smart phone app, etc.). There could also be one or more levels of an alarm or warning where the risk assessment number exceeds a risk threshold. A record of the most recent risk assessment and/or if the most recent risk assessment exceeded a predetermined risk assessment threshold, typically along with a corresponding time stamp can also be saved to non-volatile memory.

The magnitude of the energy of each RHI can be provided in any suitable units. For example, exemplary units believed to be suitable for use in equation 1 as providing impact energy equivalents include, Linear acceleration (LA), Rotational acceleration (RA), Head injury criterion-15 (HIC15), Gadd severity index (GSI), Hit severity profile (HITsp). Note that time aspect of some units, such as, for example, HIC which considers the time duration of an impact event, should not be confused with $t_n$ and $t_{n-i}$ of equation 1, which relate to the time duration between previous RHI and the most recent RHI, particularly, and most commonly, between sub concussive RHI.

As described hereinabove, HIDEN is based on the time between head impacts and the energy of each impact. HIDEN is believed to be a new metric related to brain white matter risk assessment. The HIDEN alone describes only our new understanding that both the energy and time between impacts can provide a basis for risk assessment. HIDEN is driven by the time of impacts and the energy of impacts and calculates in a new way a dose equivalent. However, we have also realized that different subgroups or subpopulations have very different risks of brain white matter injury for a given HIDEN. In other words, given the same time—energy sequence of impacts (RHI), a high school football player would have the same HIDEN as a professional NFL player. Yet, we know from our studies that the risk of brain white matter changes is likely to be very different between the subpopulations of male high school football player and profession NFL athletes. Therefore, what is needed is a way to adapt the new HIDEN to subpopulations.

Sub population function:

A sub-population function calculates a risk of brain white matter change or injury (risk assessment) based on the latest HIDEN. Sub-population functions are different for different subpopulations. While the possible variety of subpopulations can be infinite, specific more commonly used subpopulations can be studies and sub-population functions can be determined and further refined over time for certain common subpopulations. Useful subpopulations are contemplated to include gender and age. Amateur (e.g. school and college) or professional (e.g. NFL) are believed to also be common and useful subpopulations. Also, we note that different subpopulations can be characterized differently depending on an activity (e.g. American football vs. soccer vs. mixed martial arts, etc.) for which the individual is being monitored.

A sub-population function can be derived or determined from experimental observation of a number of individuals of the subpopulation. Those test subject individuals are outfitted with any suitable apparatus to measure RHI and determine HIDEN with periodic laboratory testing to determine the status of the individual's brain white matter (e.g. white matter changes or white matter injury). The HIDEN/risk assessment clinical study can be processed as other medical studies using any suitable statistical analysis. For example, we have used standard receiver operating characteristic (ROC) or ROC curves to analyze test data from amateur college athletes. Such clinical ROC techniques are well known to those skilled in the art of medical research. By comparison of control subjects, we were able to determine under what HIDEN conditions the subpopulations were more, or less, at risk of white matter injury.

In our studies, our ROC curves for both athlete subjects and control subjects were plotted by HIDEN to DTI study data for each individual. We were then able to fit a function by standard curve fitting and/or regression techniques to the ROC curve to determine a sub-population function for that population.

example: Studies of collegiate football player RHI and DTI assessments performed during at the end of a playing season led to our second embodiment of the HIDEN calculation which adds another dimension of time weighting to each RHI, the time until the end of the playing season.

Figure 13:
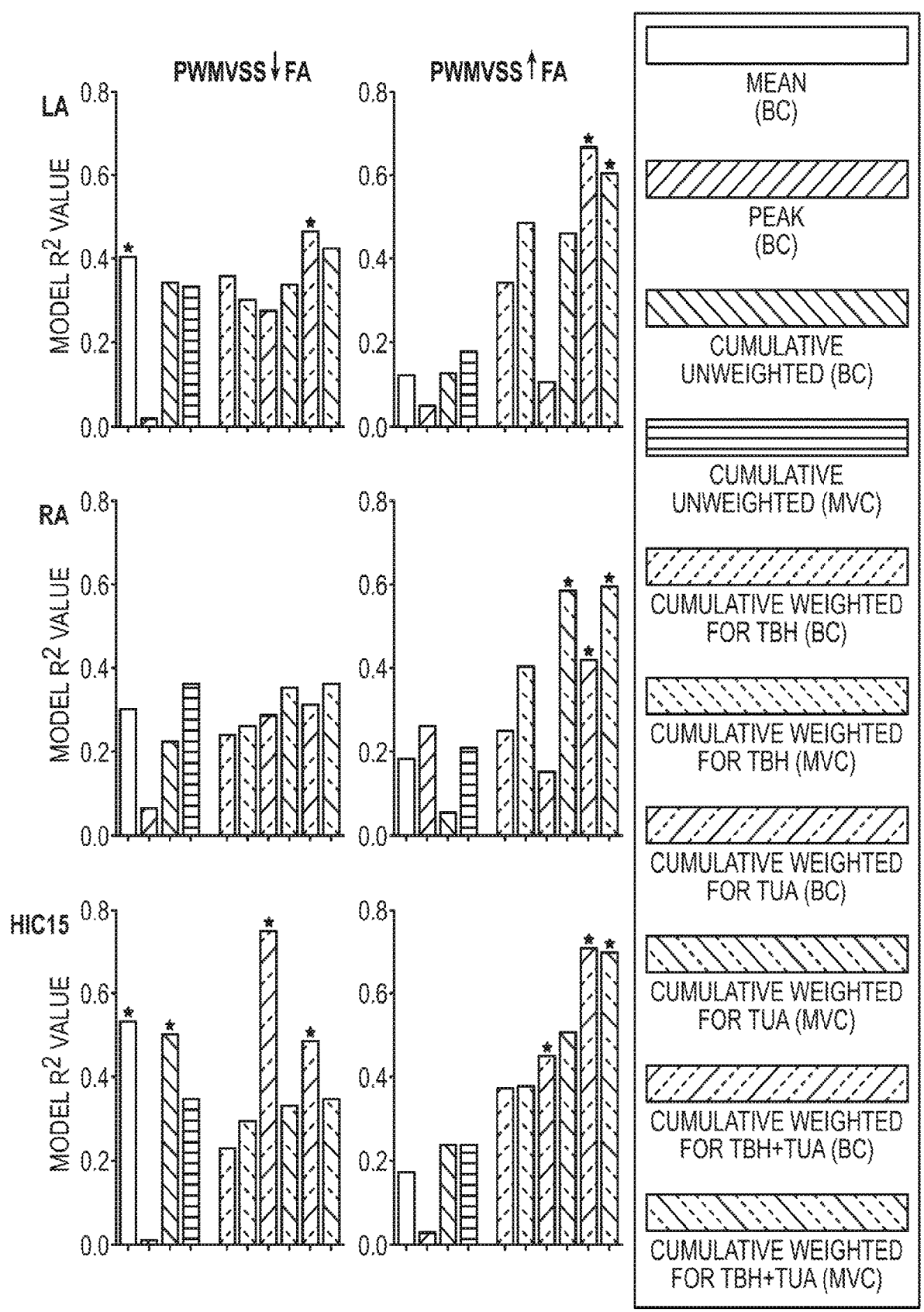
FIG. 13 shows graphs of model $R^2$ values from correlations of HIMs with pre-season to post-season changes in PWMVSS↓FA (left) and PWMVSS↑FA (right)
Figure 13:
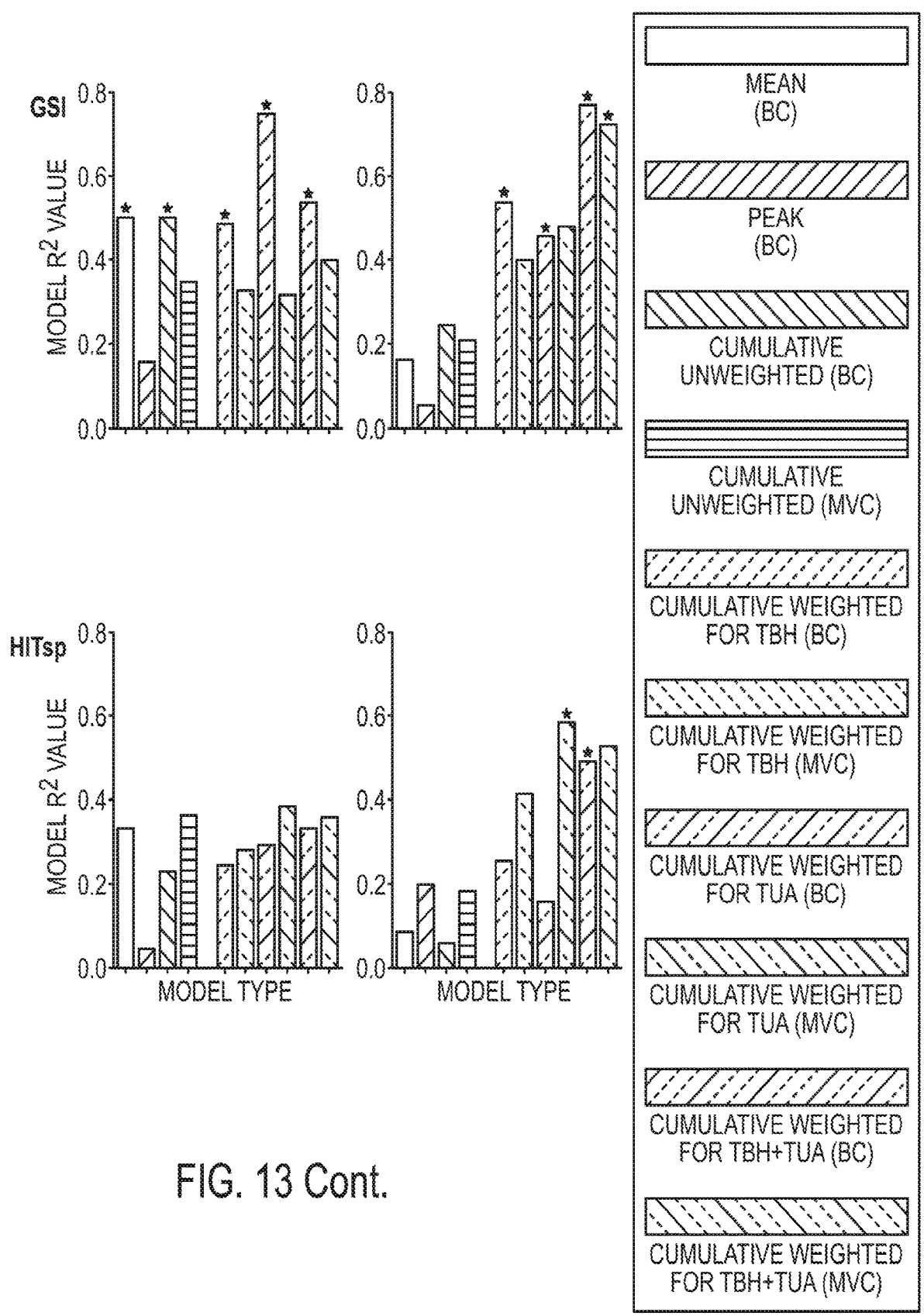

FIG. 13 shows bar graphs of model $R^2$ values (i.e., coefficient of determination) versus various data sets for five models that we tested: linear acceleration, rotational acceleration, HIC 15, Gadd severity index (GSI), Hit severity profile (HITsp). The left column of bar graphs shows the $R^2$ data for the DTI measure, proportion of white matter with significantly decreased FA. The right column of bar graphs shows the $R^2$ for the same five models for the DTI measure, proportion of white matter with significantly increased FA.

As we described in Appendix A, changes in fractional anisotropy (FA) can be seen in DTI as an FA decrease (left column FIG. 13) (↑FA), or as an FA increase (right column, FIG. 13) (↓FA). Where for example, there has been axonal loss, water is less constrained to move in a linear direction in between axons, leading to a decrease in FA (↓FA). In contrast, where there is axonal swelling, water is more constrained to move in a linear direction between axons, leading to an increase in FA (↑FA). Both axonal swelling and axonal loss are known pathophysiological stages in the process of traumatic injury to the brain.

Figure 14:
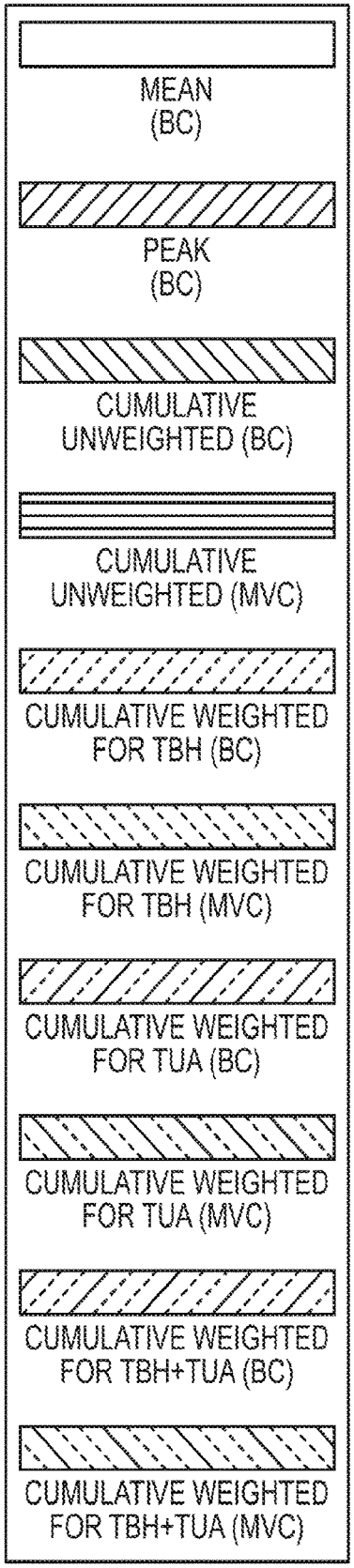
FIG. 14 shows a table of model $R^2$ values from correlations of HIMs with pre-season to post-season changes in PWMVSS↓FA (left) and PWMVSS↑FA (right)
Figure 14:
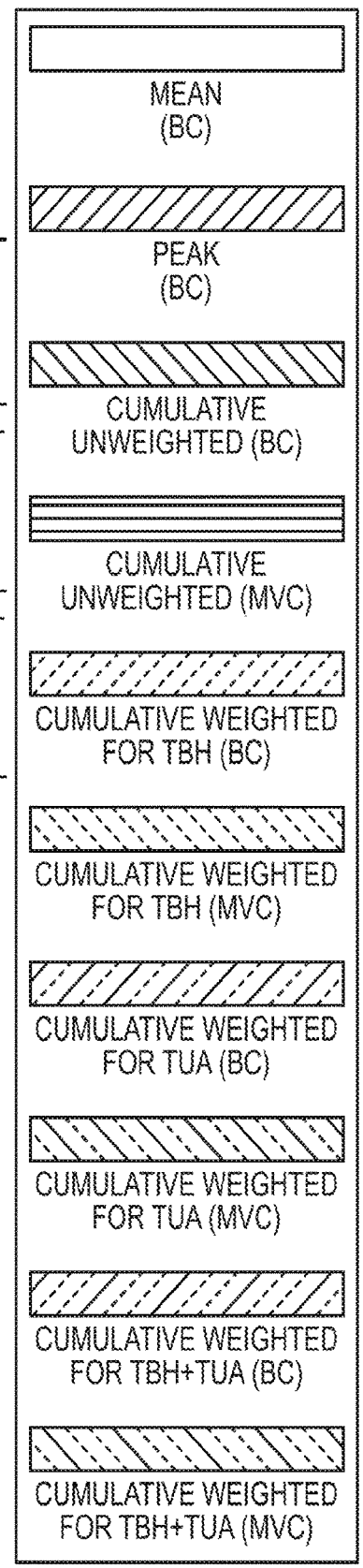

FIG. 14 is a table showing a summary of Spearman's rank-order correlation and significance values for weighted hit metrics as shown graphically in FIG. 13.

Figure 15A:
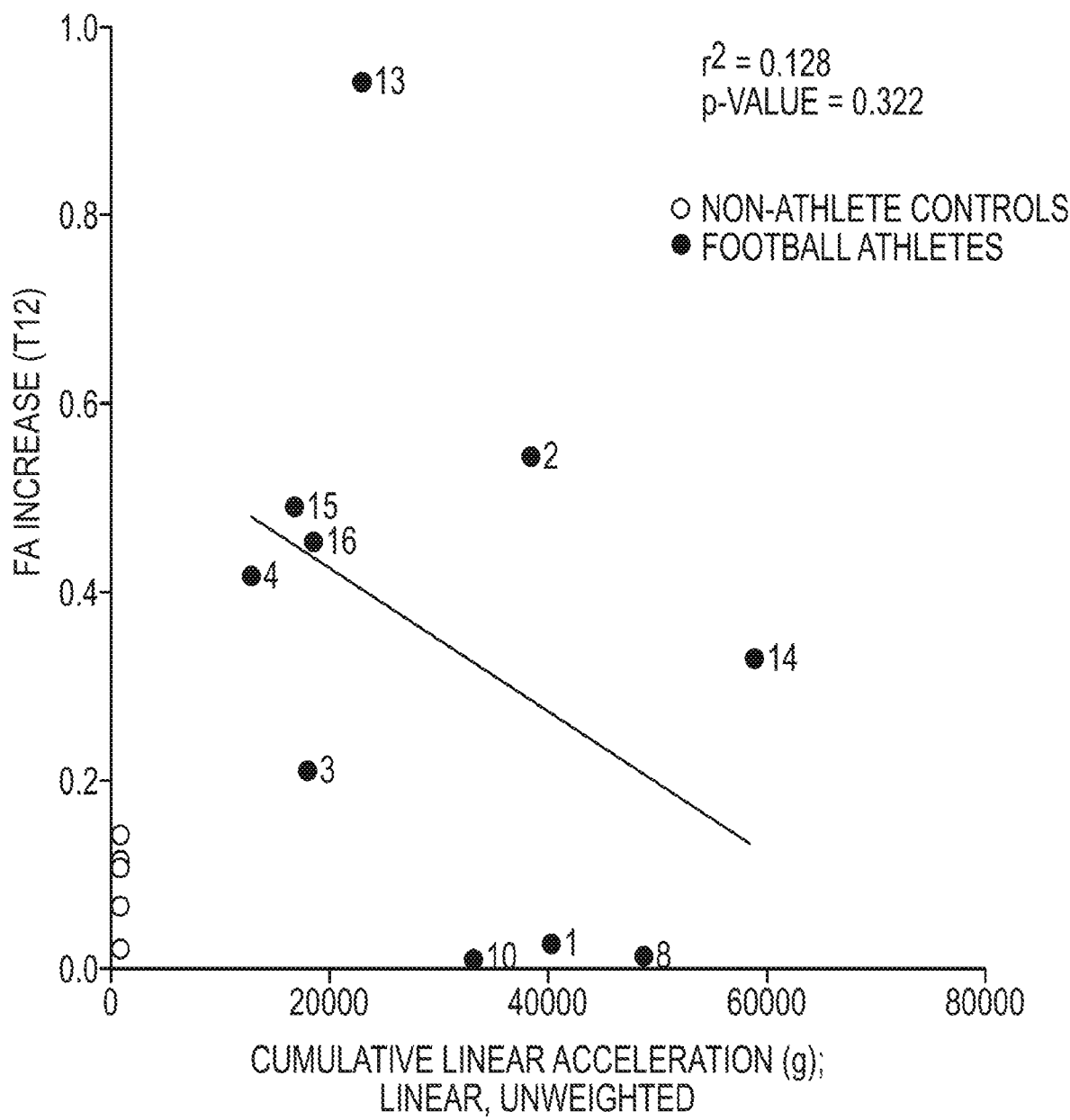
FIG. 15A shows an exemplary graph of a linear regression of un-weighted cumulative linear acceleration fit to ↑PA.

FIG. 15A shows an exemplary graph of a linear regression of un-weighted cumulative linear acceleration fit to ↑FA based on the raw data underlying FIG. 13 and FIG. 14.

Figure 15B:
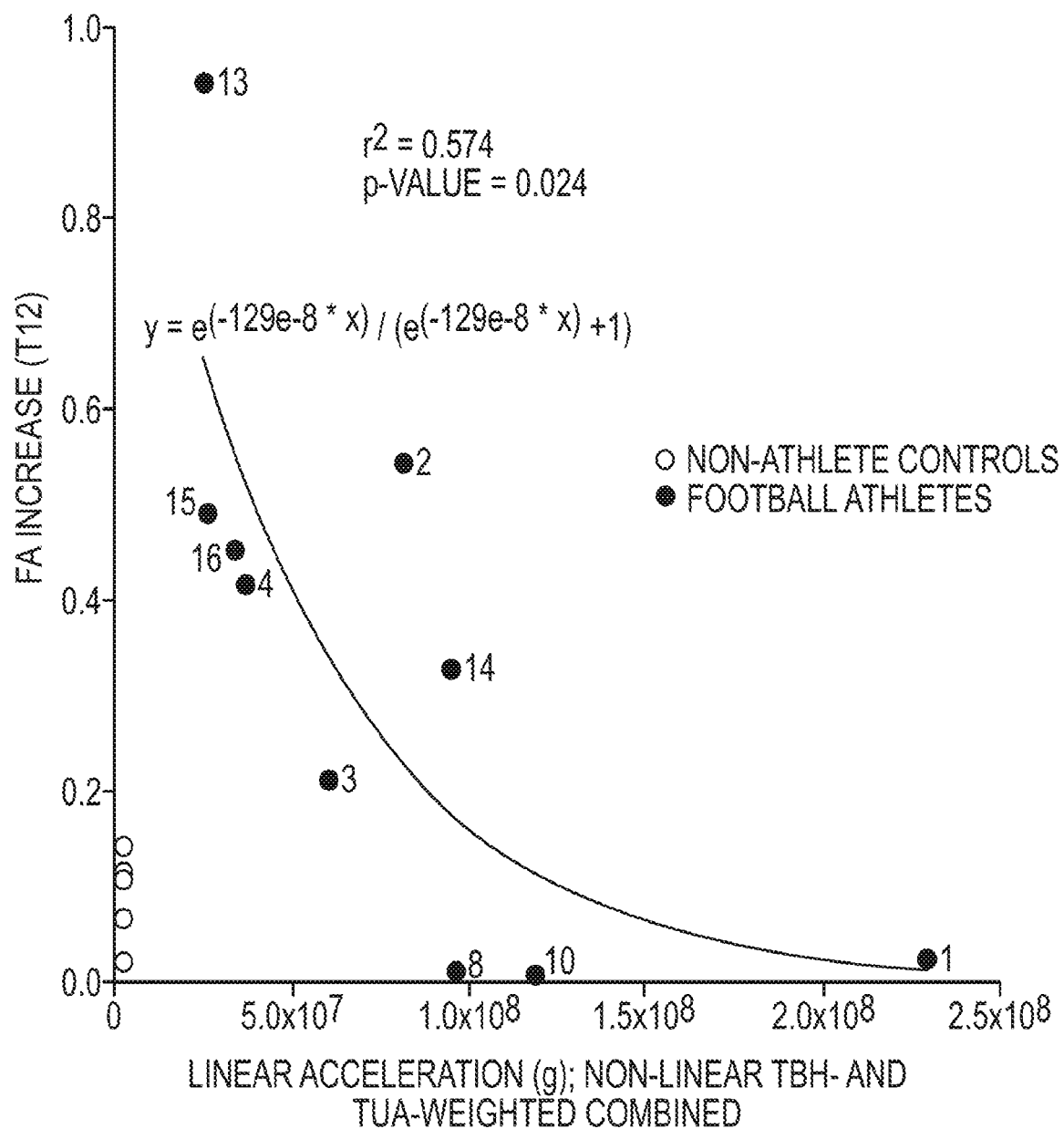
FIG. 15B shows an exemplary graph of a linear regression of cumulative linear acceleration weighted by both time between hits (TBH) and time until assessment (TUA) fit to ↑PA.

FIG. 15B shows an exemplary graph of a linear regression of cumulative linear acceleration weighted by both time between hits (TBH) and time until assessment (TUA) (analogous to EQ. 2 hereinabove) fit to ↑FA also based on the raw data underlying FIG. 13 and FIG. 14. The equation:

$$y = \frac{e^{(-1.29e-8*x)}}{(e^{(-1.29e-8*x)} + 1)}$$

is the sub-population function for the collegiate Division III players of this clinical study.

The exemplary sub-population function for collegiate Division III players was determined by a combination of helmet worn sensors (to measure HIDEN) and clinical DTI to provide the ROC curve to determine the sub-population function. However, it is contemplated that other alternatives to DTI will be found which can also be used in clinical studies to determine sub-population functions. For example, it is contemplated that blood studies or studies of other body fluids can be used to determine brain white matter changes and brain white matter injury, such as for example, our new blood analysis techniques as described in U.S. Patent Application Publication No. 20120244555 A1 related to high density lipoprotein (HDL) particles.

If HIDEN measurements become standard and routine for some subgroups, it might also be possible to supplement sub-population functions by post-mortem brain study for individual with previously recorded HIDEN data, however such studies need to be performed within an hour or two of death and therefore might be less commonly performed.

Risk assessment based on a sub-population function is based on our observation that when considering RHI, the time between hits can be used to predict and prevent white matter changes and white matter injury. Since our realization of the importance of time between hits and how shorter time between hits can lead to such changes and injury when the time is short, we have identified yet another factor to consider, the time remaining in the playing season, or for year round sports or other activities, an arbitrary period analogous to playing season (e.g., a 6 month period for a particular type of construction or other industrial worker where RHI is common).

Turning back to HIDEN, in our studies, we also considered time until assessment (TUA). The literal meaning of this term in our studies is the period of time until a next formal series of Brain DTI. As described hereinabove, unfortunately exotic DTI studies are limited to a few hospitals and research centers and are expensive and time consuming diagnostic procedures. However, in studying our post testing data and the TUA, we made another surprising realization, that we could better fit the DTI data by adding another weighting factor of how far the player was from the end of that season where they would undergo an assessment of their brain structure. In other words, while HIDEN EQ. 1 alone is useful and will be sufficient in many activities, in other embodiments, we contemplate that a HIDEN calculation further weighted by the time into the season (or, an arbitrary predetermined activity period which is analogous to a playing season) can provide more accurate HIDENs. Examples of the raw NFL data which led to this second embodiment of the HIDEN calculation are included hereinbelow in Appendix B.

In some embodiments HIDEN calculations can be further weighted by how far an individual player is into a season:

$$HIDEN_n = \sum_{i=1}^{n} \frac{ht_i}{\max(1, t_S - t_i)} + \sum_{i=1}^{n-1} \frac{ht_{n-i}\left[\frac{1}{t_n - t_{n-i}}\right]}{\max(1, t_S - t_{n-i})}$$

EQ. 2, where, $HIDEN_n$ is the head impact dose equivalent number following the most recent head impact, now also as a function of time into the playing season (or, equivalent period of time), $ht_i$ is the magnitude of the energy of the most recent head impact, $ht_{n-i}$ is the magnitude of the energy of the n−i previous head impact, n is the total number of RHI, $t_s$ is the time to the end of the current playing season, and $t_i$ is the time of the most recent head impact. It can be seen that as $t_s-t_i$ becomes smaller (the RHI are occurring closer to the end of the season, where RHI are more heavily weighted). Thus, for example, where the HIDEN calculations are further weighted by how far an individual player is into a season, EQ. 2 can be substituted for the EQ. 1 of FIG. 3, 302.

Display and Reporting: The display and reporting means 103 of a system 100 for measuring and recording HIDEN from RHIs for at least one individual can be of any suitable type. The display could provide notice of a risk assessment value above a risk assessment threshold for each individual monitored person. The complexity or detail of displayed data or the exact nature of a threshold warning or alarm is unimportant.

In some embodiments, it is contemplated that there could be a complete package worn by an individual including at least one sensor 101, processor 102, and a display and reporting means 103. For example, a helmet including all three blocks could include at least one indicator, such as a bright light to show that the individual's successive RHI magnitude time weighted risk assessment has exceeded a predetermined threshold for that individual. In the context of school children playing in an organized or unorganized activity area, other players and/or supervising adults on seeing the visual indication of the child exceeding the pre-determined HIDEN value could pull the child from play.

Such fully integrated wearable systems (e.g., helmet mounted) might also be useful for military training exercises where individuals (with or without previously determined risk assessment threshold values) might come together from various posts for a relatively short duration military exercise or training activity.

In other embodiments, where at least one sensor 101 are worn by the individuals and can convey data by any suitable wired (less likely except possibly in some medical R&D studies, because of the needed tether) or wireless means. Wireless means comprises any suitable form of communications including most typically radio frequency (RF) means, although there can be optical transmitters which may be suitable to convey sensor data from an individual to a processor 102. Or, the processor can be included with a wearable system, and raw RHI time stamped data (e.g., by any suitable clock or clock receiver (e.g., GPS derived time) in the wearable system) and/or computed HIDEN data sent from the player's wearable system to a display and reporting means 103. Where the processor 102 is onboard the individual's wearable gear, RHI and/or HIDEN alarm data can be directly sent to any suitable display and recording system 103. For example, an individual's system can report to a portable platform, such as, for example, a smart phone, tablet, notebook computer, laptop computer, etc. Also, with the growing presence of WiFi, WiMax, or equivalent wireless network access, in some embodiments, an individual's wearable system (with or without an on-board processor 102) can report data wirelessly via a computer network connection to a remotely located computer (with or without an on-board processor 102) and/or display and reporting means 103.

Figure 2A:
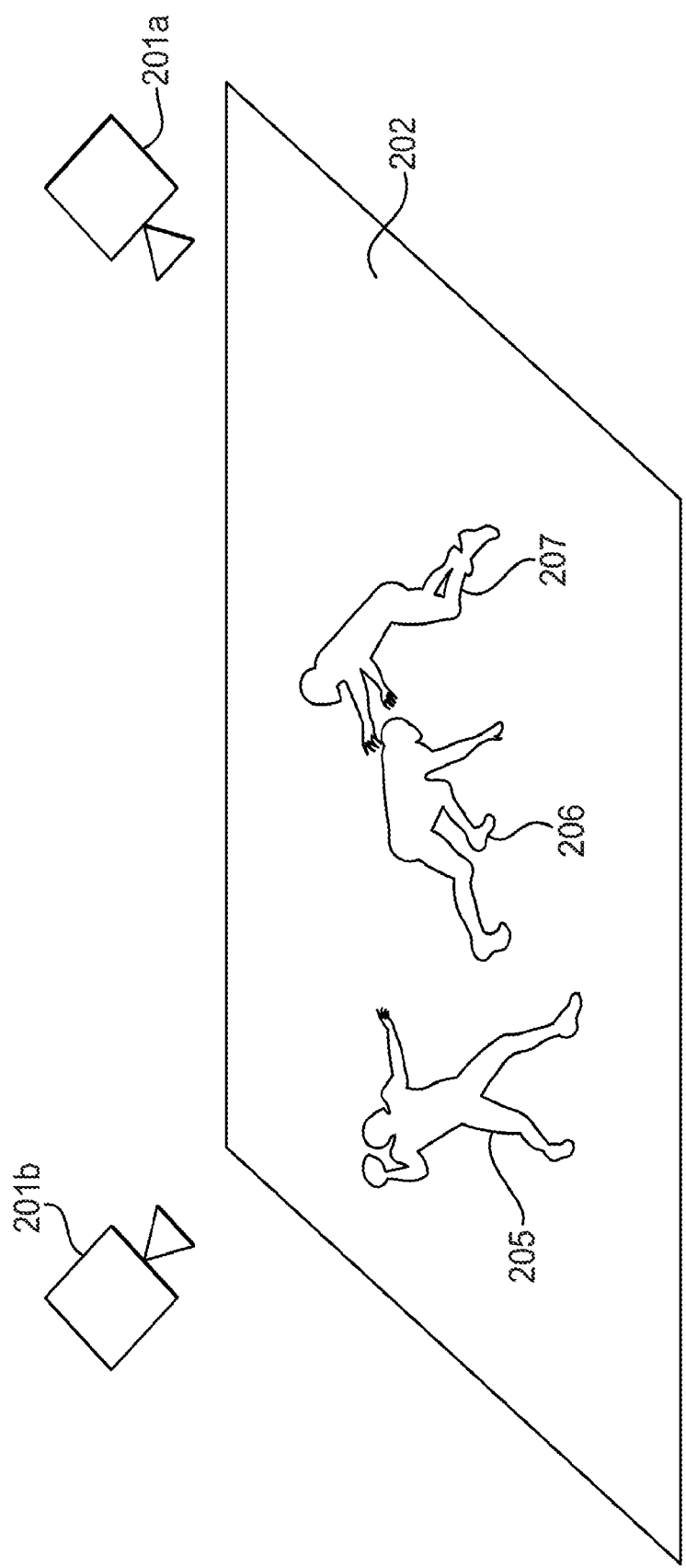
FIG. 2A shows a simplified block diagram of a sensor means of FIG. 1 based on cameras viewing an athletic field.

In other embodiments, it is contemplated that RHI data for individuals can be derived from images taken of at least one individual by at least one remotely located imaging device, such as at least one camera. FIG. 2 shows a simplified illustration one exemplary camera based system where three individuals, 205, 206, and 207 are shown on a playing field 202. Images from either or both of cameras 201a and 201b through image processing techniques can determine a head contact between individual player 206 and individual player 207. The magnitude of the impact can be estimated, for example, by calculation of the rate of approach by use of successive video images just before the RHI event. The RHI event can also be time stamped with reference at least one video frame where the RHI event took place. Moreover, impact energy can be computed or refined by the known body mass of individual player 206 and individual player 207. In some embodiments, in conjunction with such video sensing of individual RHIs, players might have at least one index on their body wear or helmets to facilitate image processing. Such an index or marker can be used to improve the calculation of pre-impact velocities for the calculation of RHI impact magnitude (e.g., impact energy).

In some embodiments, there could be redundant HIDEN measurements, such as, for example, player worn at least one sensor 101 as well as remote sensing cameras as at least one sensor 101, such as for R&D system development or high reliability and fault tolerant HIDEN measurement through redundancy. However, typically where at least one sensor 101 are provided by remote sensing (e.g., cameras) there are can be now body worn sensors by individuals. With the possible exception of at least one remotely visible marker (e.g., optical markers) a player in such a remote sensing HIDEN system would not need to have any wearable sensors or wearable electronic systems.

Figure 2B:
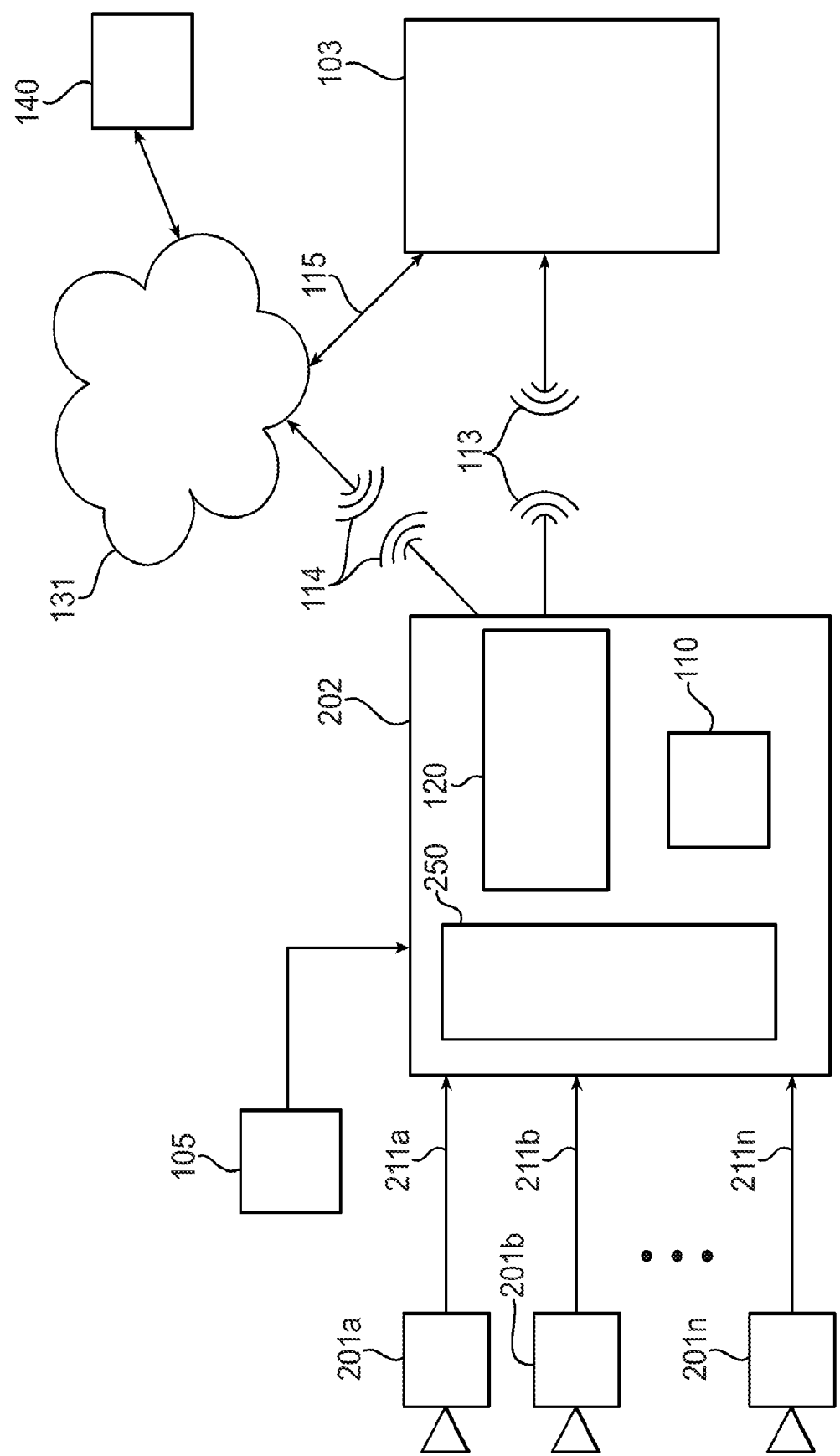
FIG. 2B shows a simplified block diagram of exemplary hardware suitable for use with the system of FIG. 2A.
Figure 2C:
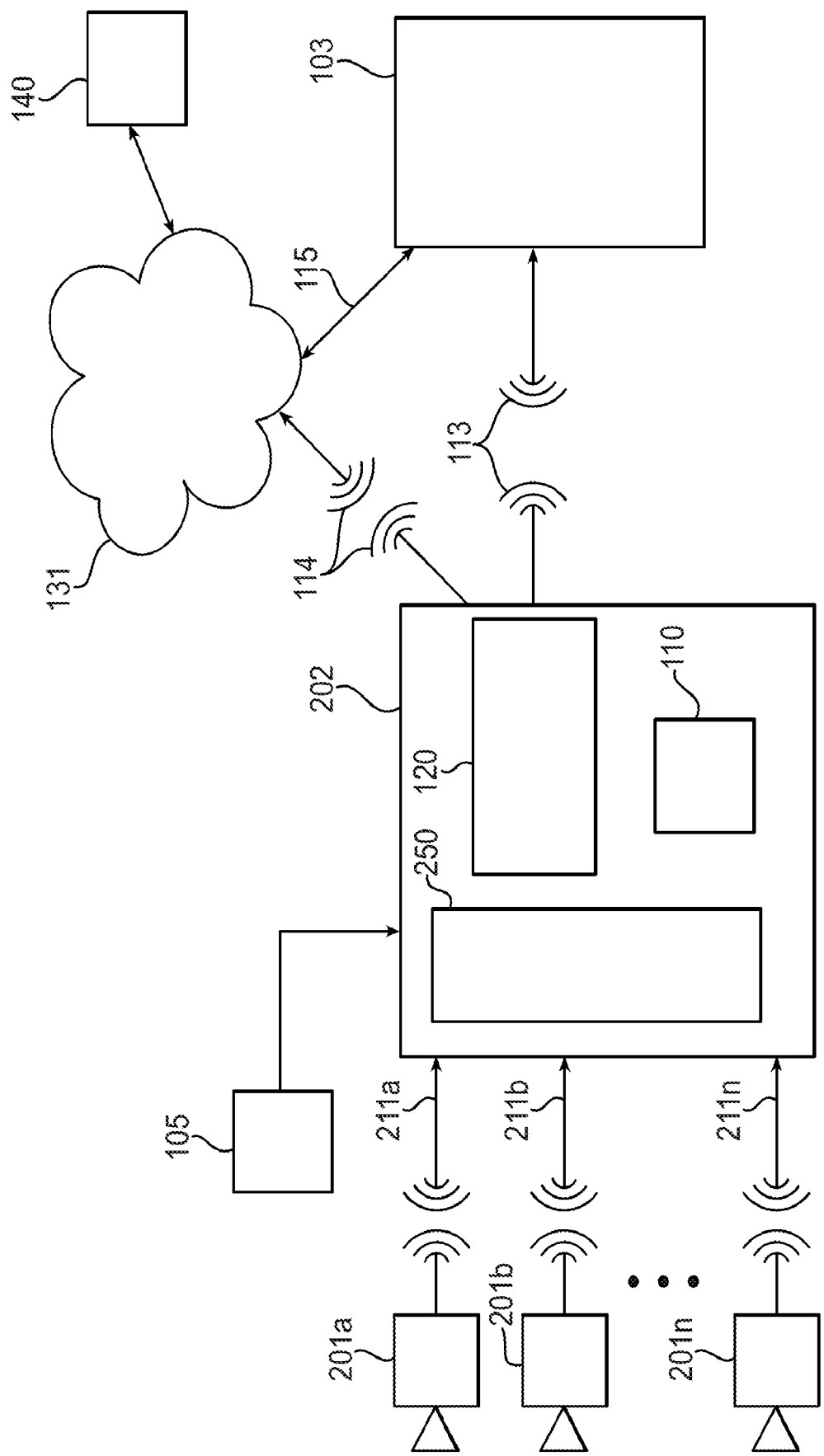
FIG. 2C shows another simplified block diagram of exemplary hardware suitable for use with the system of FIG. 2A.

FIG. 2B shows a block diagram of an exemplary embodiment of a HIDEN system and method where the cameras provide all of the sensory input, in the absence of individually worn sensor systems 101. As in FIG. 2A, at least one camera 201 (e.g., cameras 201*a*, 201*b* . . . 201*n*) image the location where at least one individual will likely experience at least one RHI, such as, for example a college or professional playing field. At least one camera 201*a* to 201*n* can be communicatively coupled to computer 202 by any suitable wired or wireless means. As shown in the exemplary embodiment of FIG. 2C, cameras 201*a* to 201*n* can be WiFi cameras.

The RHI events for at least one player are detected by an RHI image process 250. Imaging processing is well known in the art and can be accomplished in any suitable way. For example, image processing can identify the heads of two or more players on a playing field and follow at least one of: position, velocity, and acceleration of the heads and realize by position when there is an RHI event. Players heads can also be made more easily identifiable to RHI image process 250 by some marking, for example, on each player's helmet. Such markings can be as simple as a number or other indicia to ID each player. Or, in some embodiments there can be other markings, such as dots or lines visible to the cameras, but not necessarily visible to spectators, which can assist RHI image process 250 to determine head position and rotation. In some embodiments, there can be markers elsewhere on an individual's body to help RHI image process 250 identify head motion (e.g., lateral and/or rotational) with respect to the individual's torso. Additionally, movements of marked extremities, such as arms or legs, can facilitate or provide redundant data to check inferences by RHI image process 250 of the energy (e.g., g forces) of each RHI event observed and calculated by RHI image process 250.

In camera only embodiments, computer 202, FIG. 2B is closer to the function of the display means 103 of FIG. 1. However, there can be the same variation of embodiments as described with respect to FIG. 1. The main difference between camera only embodiments (e.g., FIG. 2A, FIG. 2B) and body worn sensor embodiments (FIG. 1), is that there would typically be no body worn computers for the purpose of processing data directly from the body worn sensor system 101, FIG. 1 of each individual. On the other hand, there still could be simple display devices 103 as a light on a player's helmet. In such embodiments, now the helmet would have a wireless means to receive HIDEN information (or at least that the individual's HIDEN has exceeded a risk assessment threshold from an RHI event) and enough local electronics (typically including a microcomputer based helmet worn system) to receive notice to that individual player's helmet worn system to turn on a local light (e.g., a high brightness LED, flashing or steady illumination). Such remotely (wireless) activated technologies (e.g., to light a LED) are well known in the art of computer science and electronics.

GPS or Other Electronic Position Locating System: As described hereinabove, a wearable GPS can provide an accurate time-stamp for an RHI event. A wearable GPS, or any other suitable position locating system (e.g., WiFi position location) can also be used to enhance or measure velocity determination prior to an RHI event as determined by any suitable means (e.g., by at least one sensor 101 worn by the individual and/or by any suitable remote sensing means (e.g., at least one camera or any other suitable remote sensing means of an RHI event). While a GPS time stamp is convenient, we note that there is no particular advantage to the accuracy of the time stamp and that any other conventional time stamp means, such as for example, a clock in the apparatus worn by the player and/or in a central unit that monitors at least one player, such as by wireless means is also suitable to time stamp RHI data.

Figure 4A:
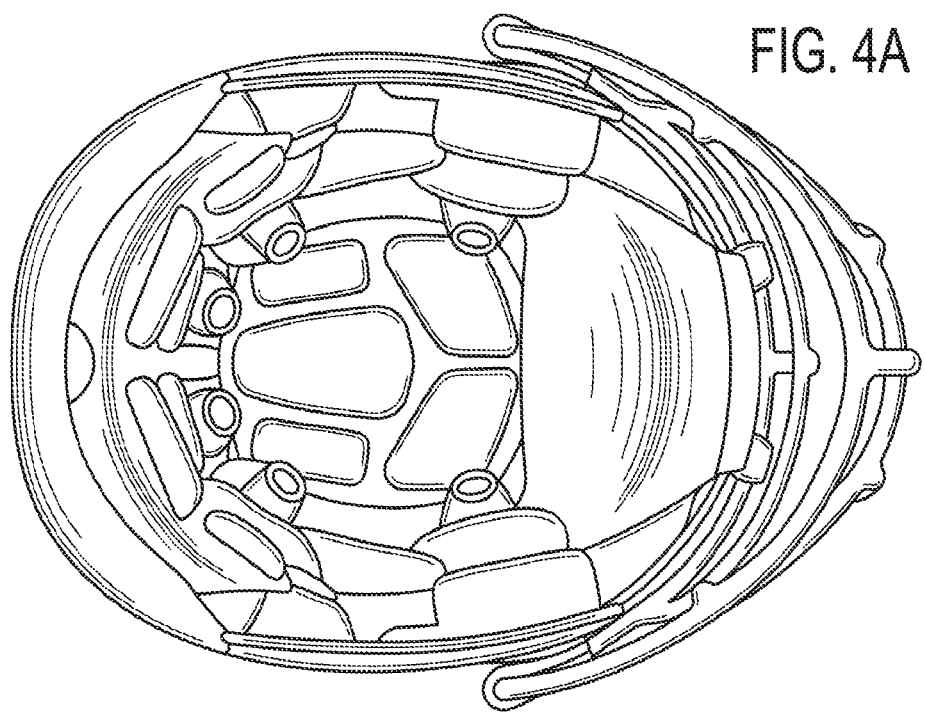
FIG. 4A shows an illustration of an exemplary Riddell helmet outfitted with sensors.
Figure 4B:
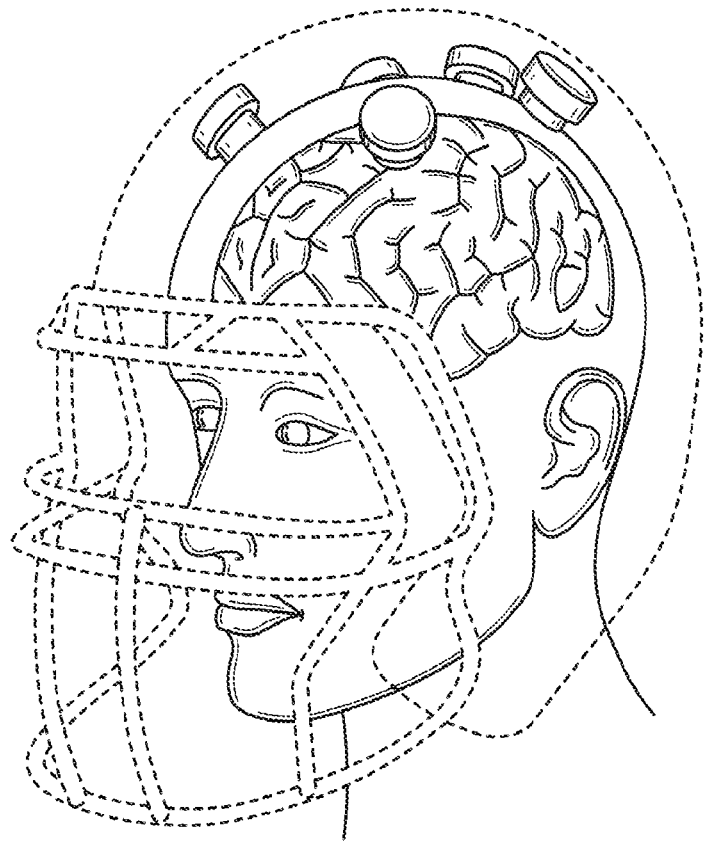
FIG. 4B shows a cutaway illustration of a Riddell sensor system placed over a player's head and brain.
Figure 4C:
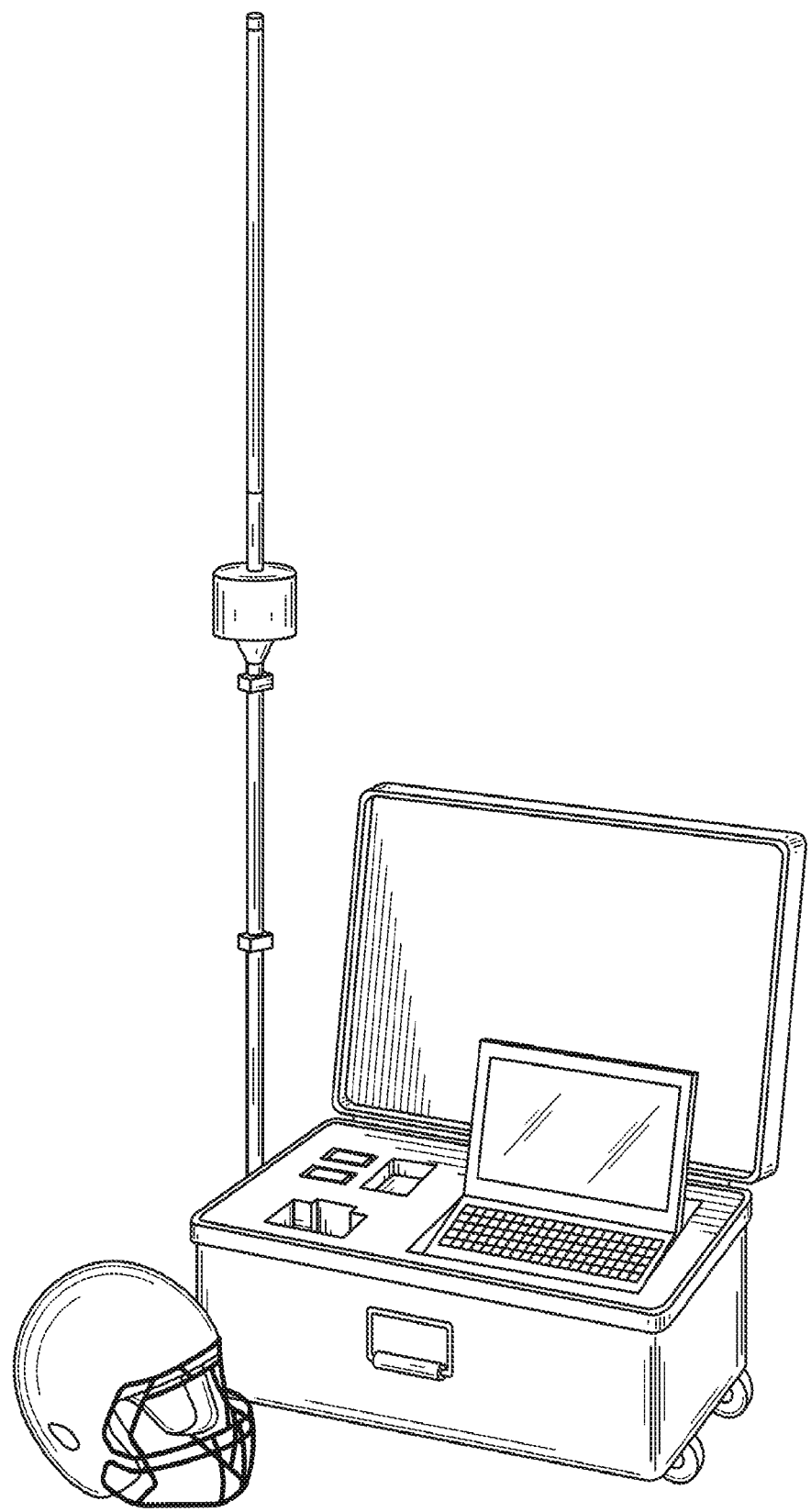
FIG. 4C shows an illustration of a typical wireless Riddell multiplayer system.
Figure 5B:
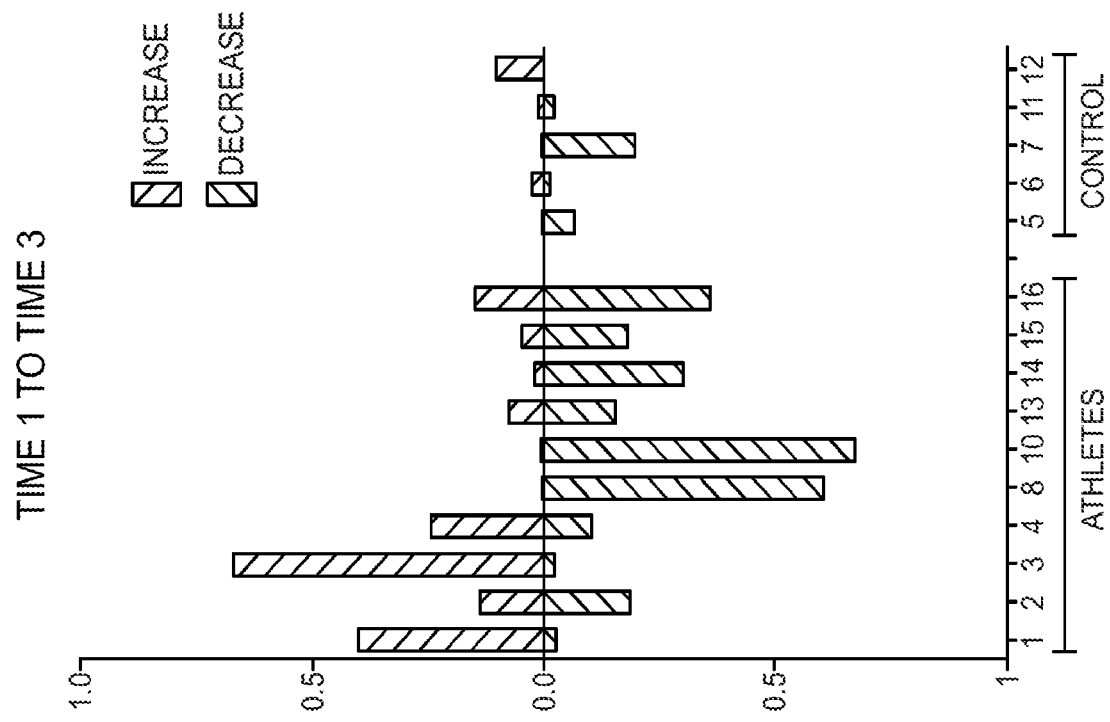
FIG. 5B shows a bar graph of percentage of white matter voxels in each individual subject for Subject-specific DTI changes in FA from Time 1 to Time 3.
Figure 5A:
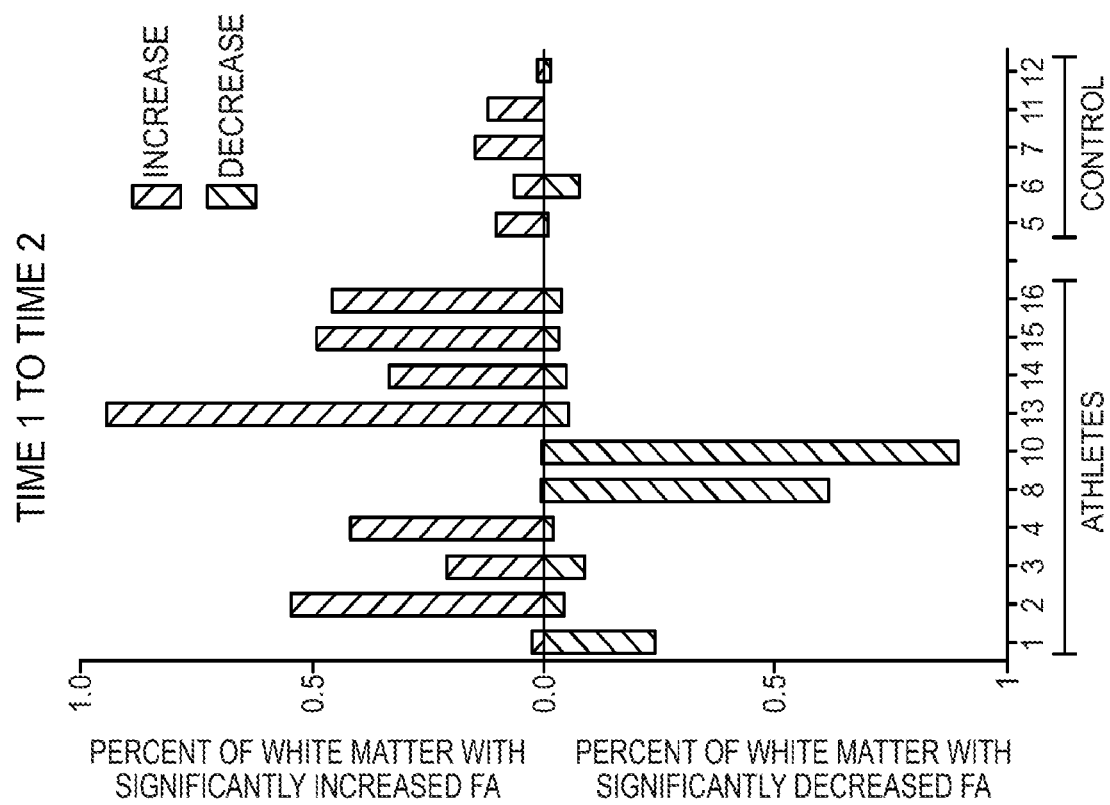
FIG. 5A shows a bar graph of percentage of white matter voxels in each individual subject for Subject-specific diffusion tensor imaging (DTI) changes in fractional anisotropy (FA) from Time 1 to Time 2.
Figure 5D:
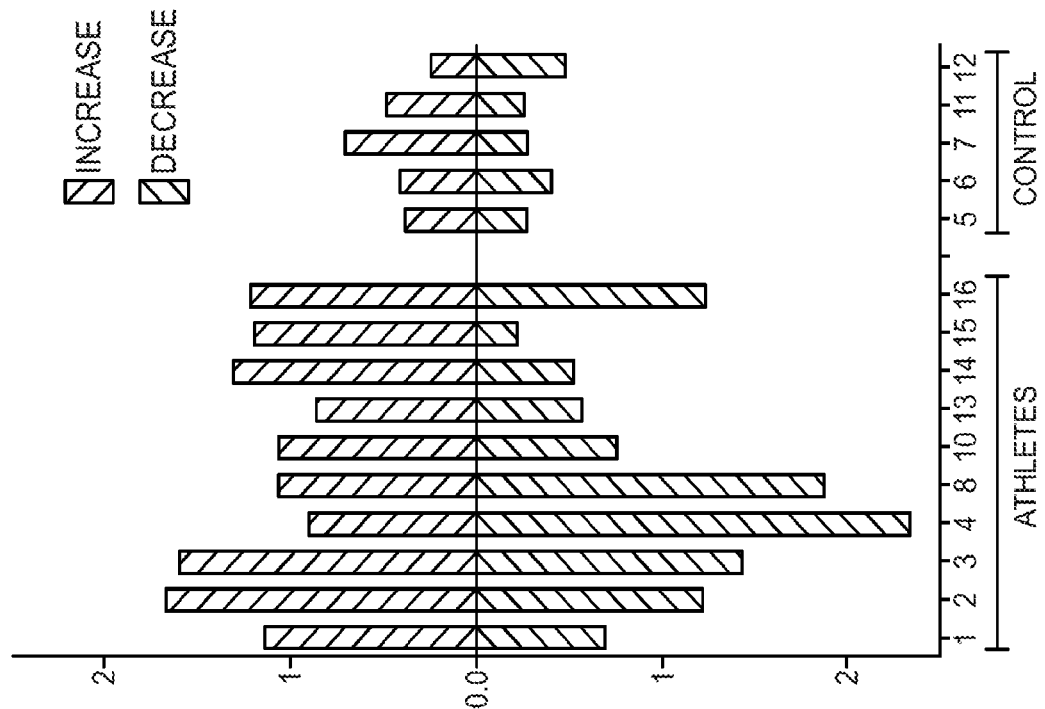
FIG. 5D shows a bar graph of percentage of white matter voxels in each individual subject for Subject-specific DTI changes in MD from Time 1 to Time 3.
Figure 5C:
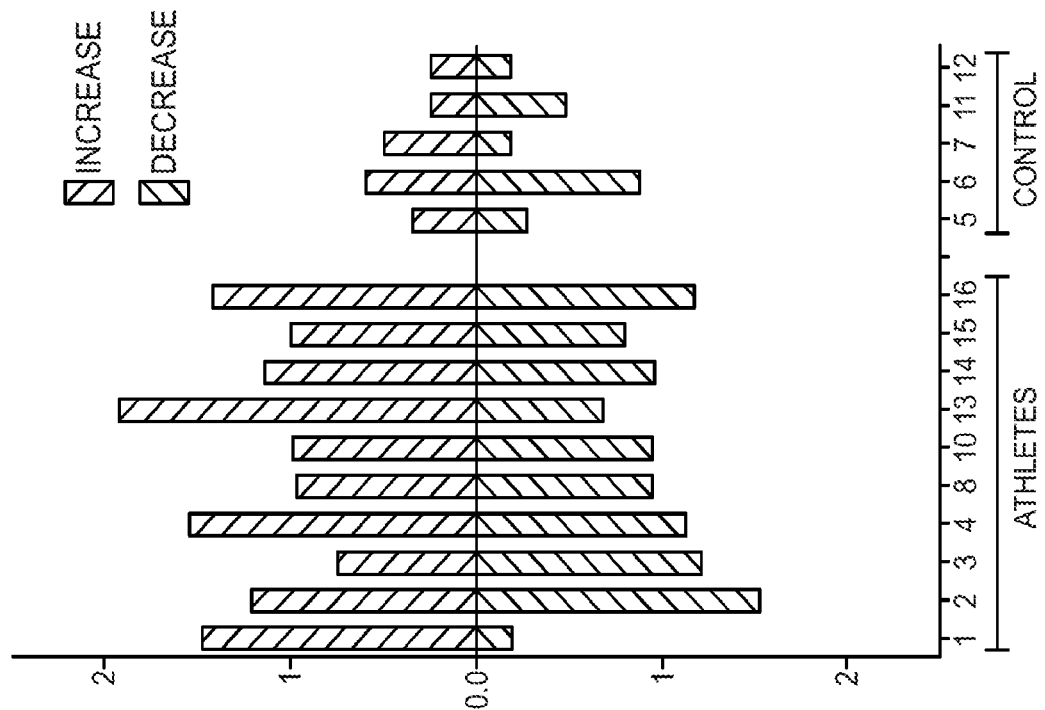
FIG. 5C shows a bar graph of percentage of white matter voxels in each individual subject for Subject-specific DTI changes in MD from Time 1 to Time 2.
Figure 6A:
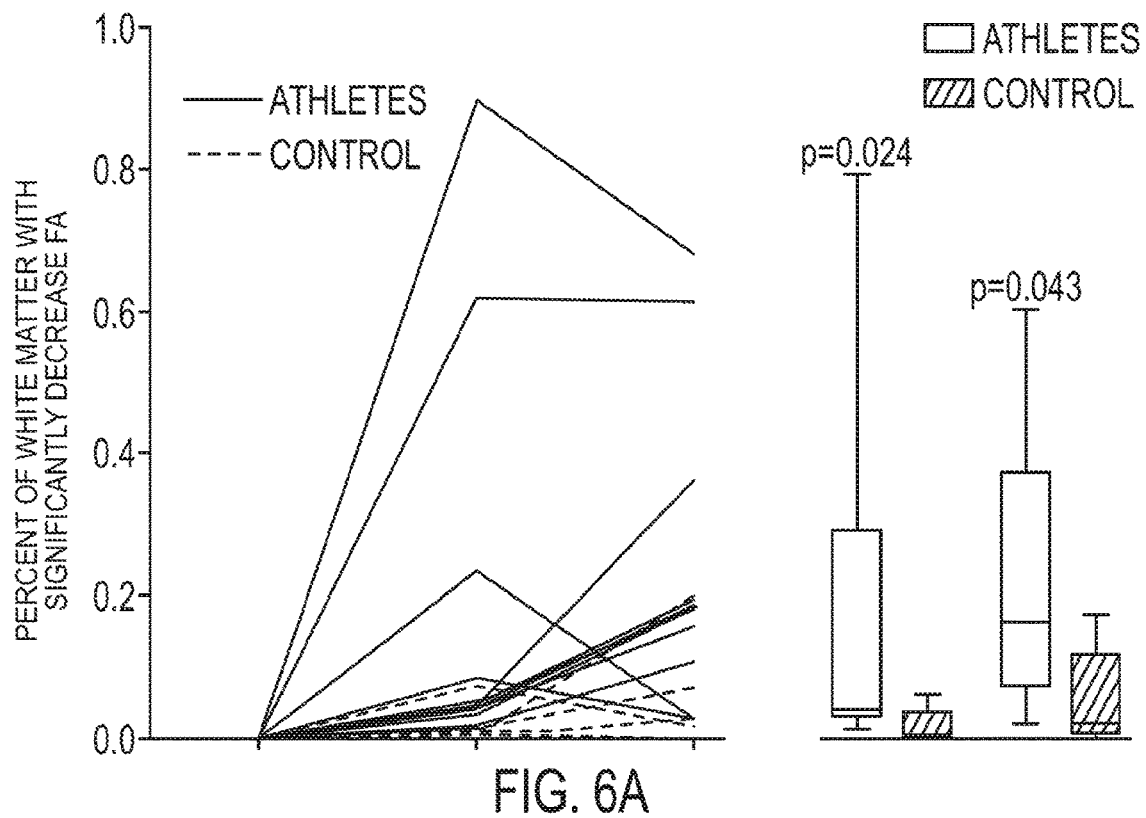
FIG. 6A shows a line graph of percentage of WM voxels in each athlete (solid lines) and each control (hatched line) with significantly decreased FA from Time 1 to Time 2.
Figure 6B:
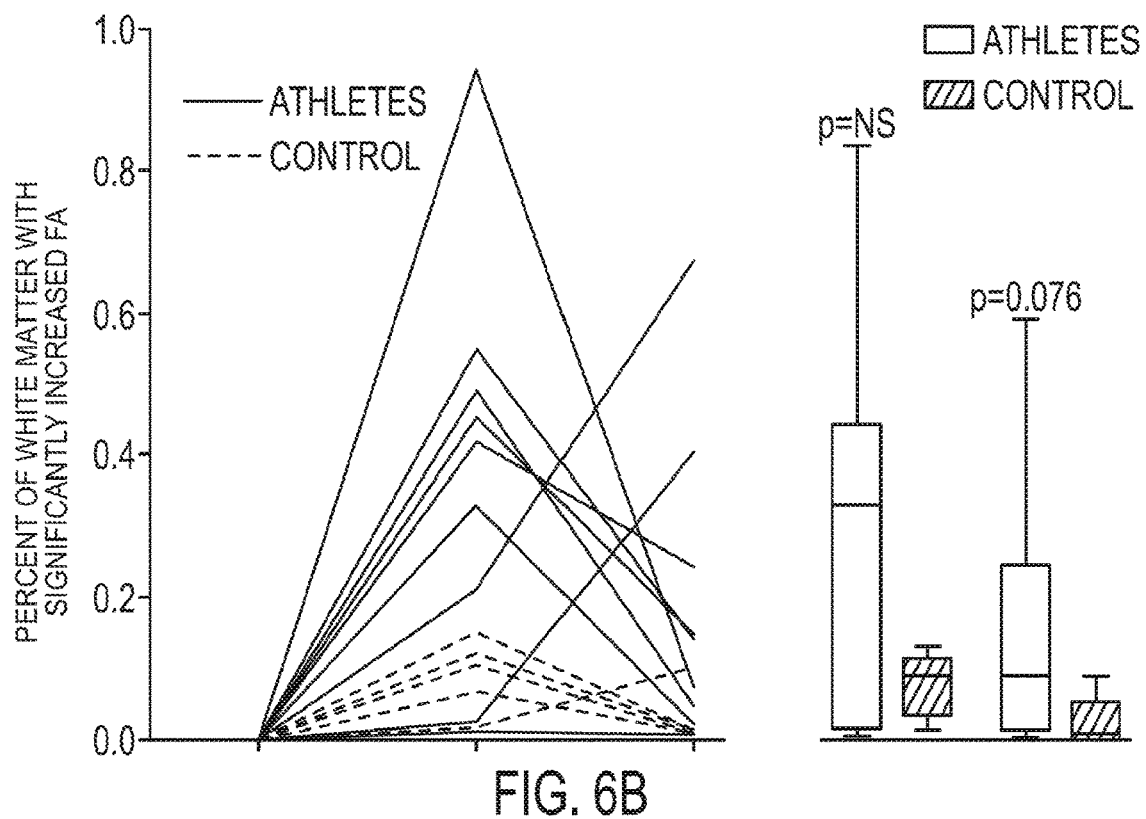
FIG. 6B shows a line graph of percentage of WM voxels in each athlete (solid lines) and each control (hatched line) with significantly increased FA from Time 1 to Time 3.
Figure 6C:
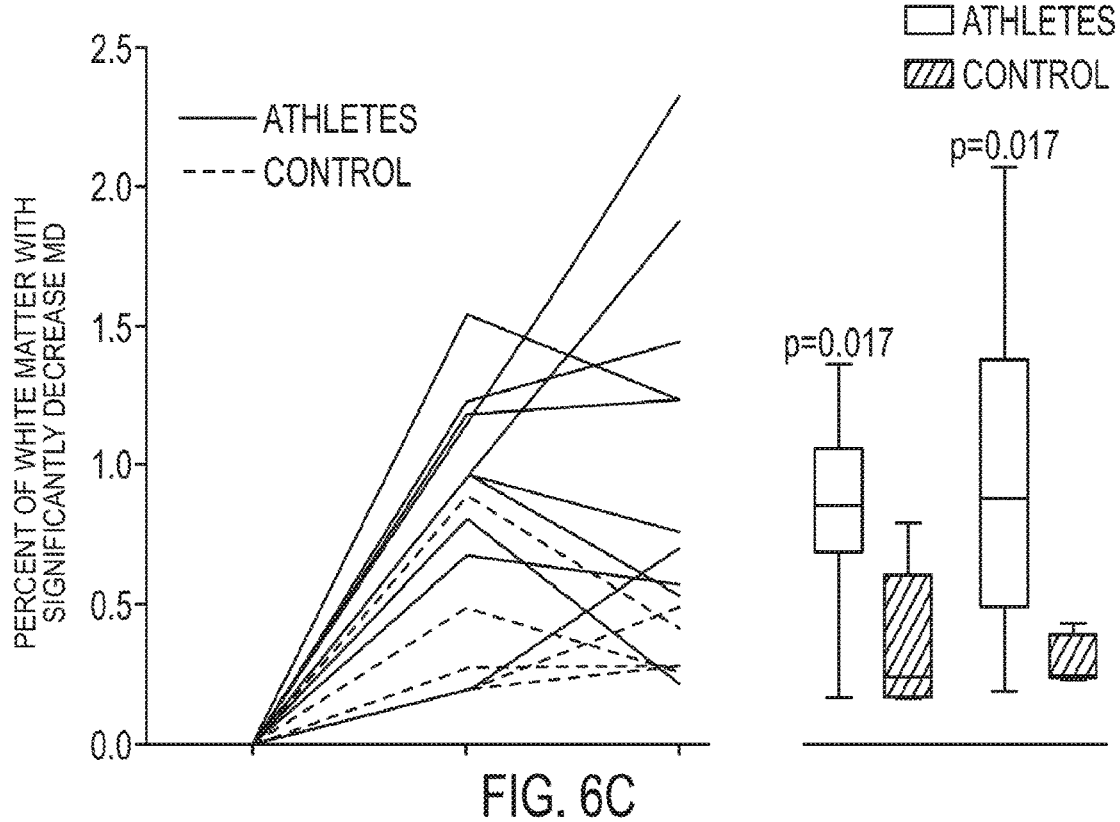
FIG. 6C shows a line graph of percentage of WM voxels in each athlete (solid lines) and each control (hatched line) with significantly decreased MD from Time 1 to Time 2.
Figure 6D:
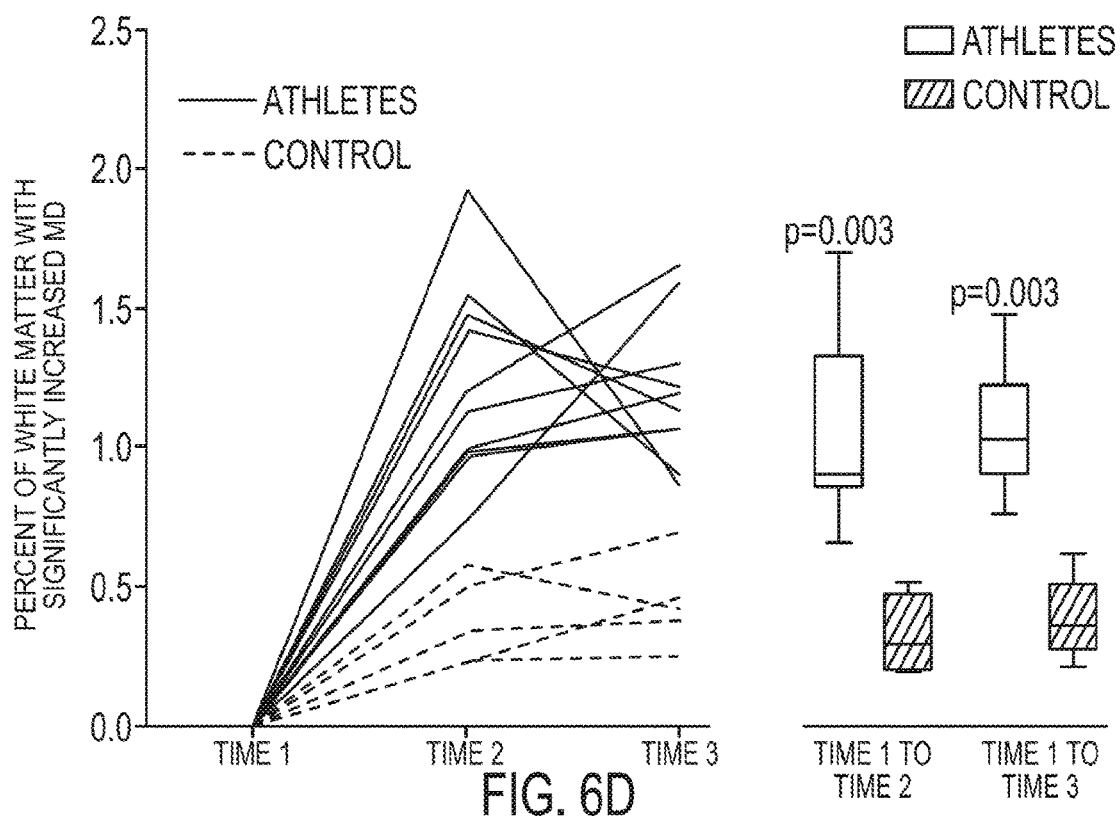
FIG. 6D shows a line graph of percentage of WM voxels in each athlete (solid lines) and each control (hatched line) with significantly increased MD from Time 1 to Time 3.
Figure 8:
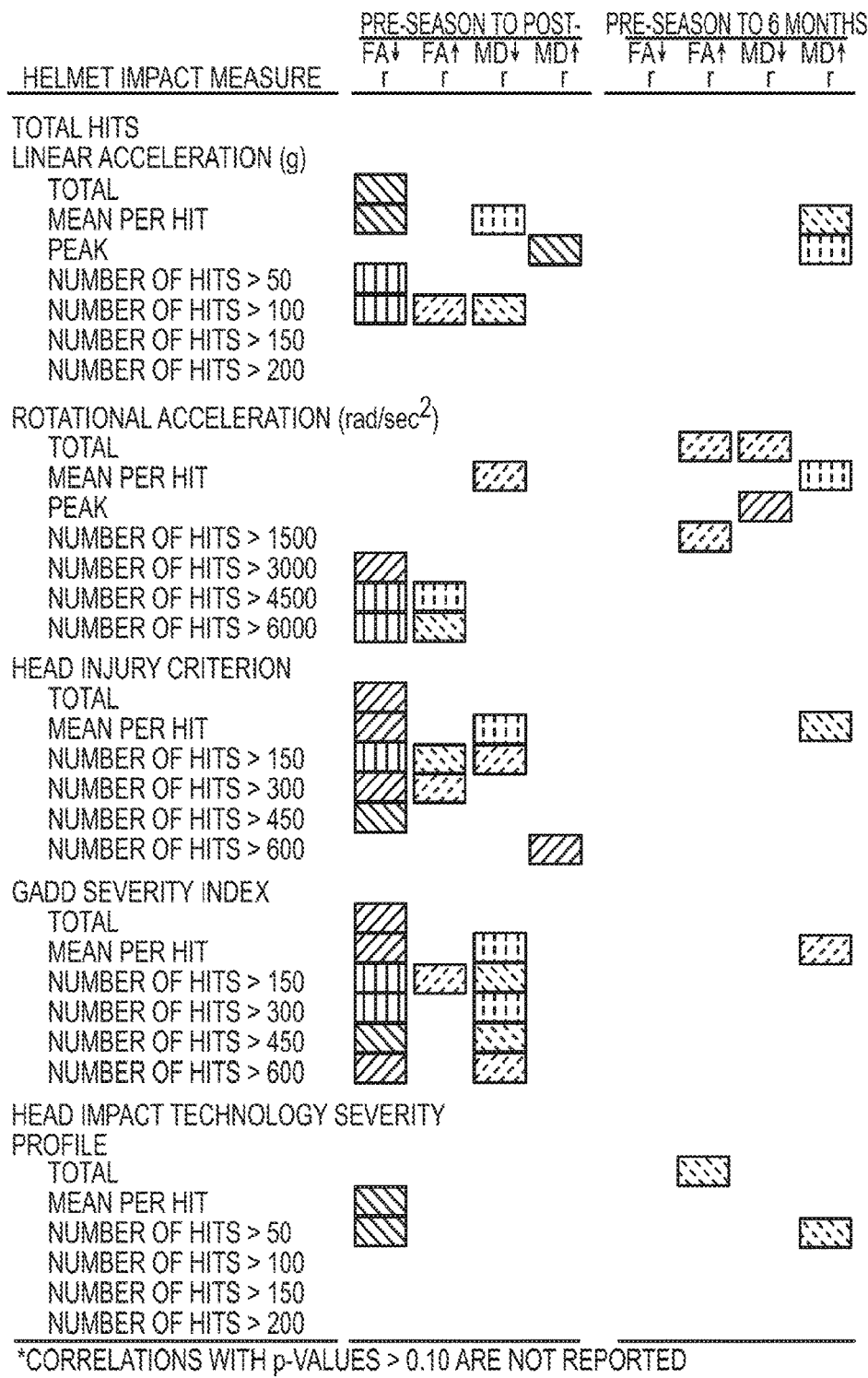
FIG. 8 shows a heat map display of correlations between helmet impact measures and DTI changes between pre- and post-season (T1 to T2), and pre- and 6 months post-season (T1 to T3).
Figure 9:
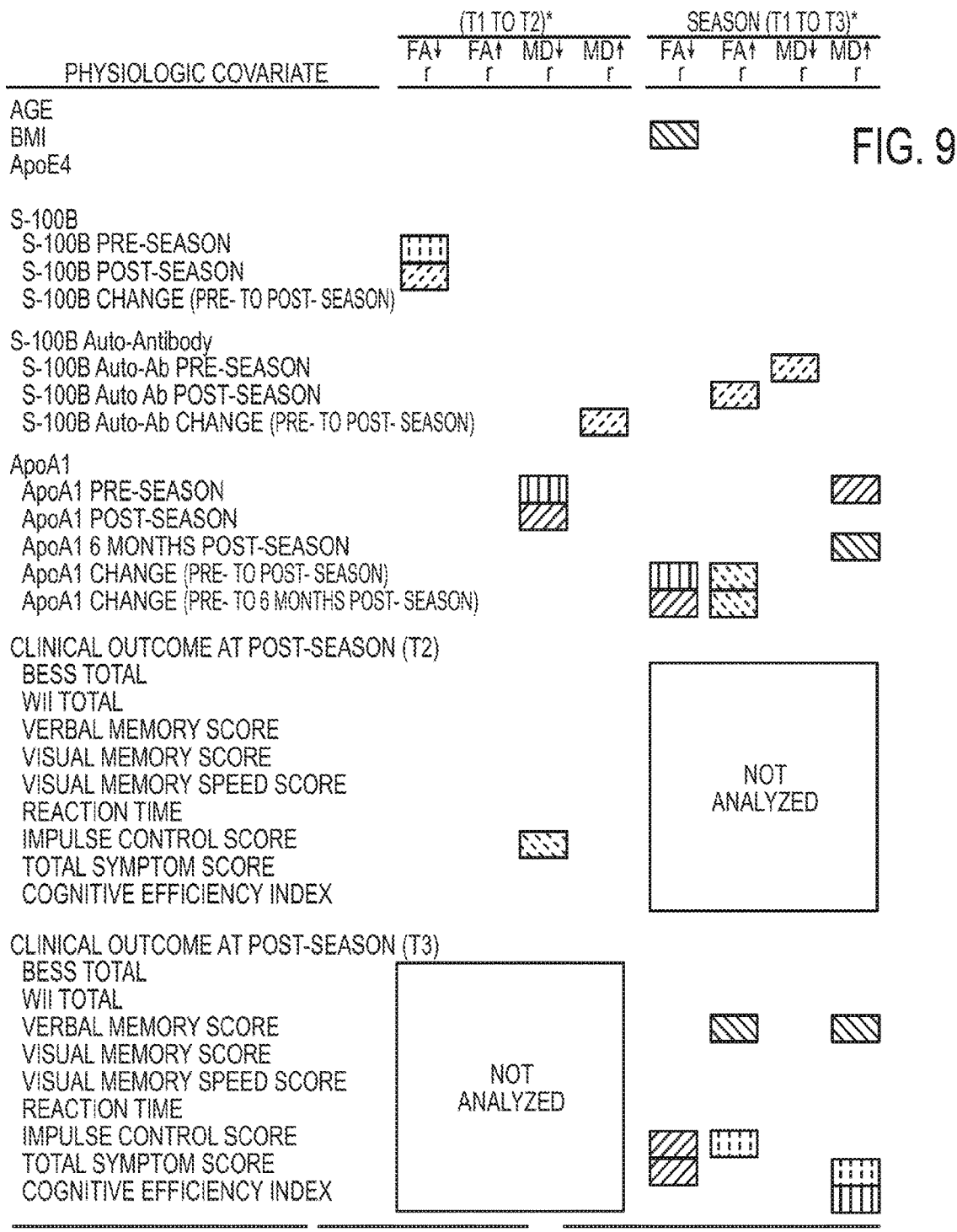
FIG. 9 shows physiologic and clinical correlations of DTI changes among athletes.

Testing apparatus: Testing was done generally with a group of college football players and non-athlete students as described in Appendix A. We used the Riddell helmet mounted sensor system to record raw RHI data. Our surprising realization of the far lower thresholds for brain white matter change and brain white matter injury and the need for a new dose equivalent process for RHI white matter related injury risk management, came from the analysis of the Riddell sensor system data combined with diffusion tensor imaging (DTI), physiologic, cognitive, and balance testing at pre-season (Time 1), post-season (Time 2), and after 6-months of no-contact rest (Time 3). FIG. 4A shows an illustration of an exemplary Riddell helmet outfitted with sensors. FIG. 4B shows a cutaway illustration of a Riddell sensor system placed over a player's head and brain. FIG. 4C shows an illustration of a typical wireless Riddell multiplayer system.

Example: FIG. 12 shows two tabulated examples of a hypothetical HIDEN calculation based on hypothetical RHI data for a player participating in a fast paced sports activity. In the upper data set, the player has 6 RHI events in about an hour (~3522 seconds total period). An un-weighted sum of total hits comes to about 208 g's. Because the hits are spaced apart by minutes and tens of minutes, the weighted sum is also about 208 g's. Note also that such hits on the order of 30 or 40 g's, are well below the energy normally associated with a concussion. By the common wisdom of those skilled in the prior art, such minor hits, are considered to be relatively safe. Now, turning to the lower set of data, the same six hits (RHI) have the same magnitude of energy of each of the six exemplary hits in the upper data set. What is different is that now the hits come in rapid succession, and within a total time period of about less than five second 11 s.

Helmet warning lights: In some embodiments, lights on head worn gear visible to at least one person watching an individual who might be subject to RHI, as have been used in the prior art to indicated a potentially concussive of highly energetic RHI, can now be used alternatively to illuminate on a HIDEN which causes a risk assessment in excess of a predetermined risk assessment threshold, rather than only illuminating based on a most recent hit based on the energy of that single hit.

Unfortunately, there might be situations where at least one immature individual intentionally tries to cause RHI to try to illuminate the light worn by an individual for a show of bravado. Therefore, there can also be embodiments where there is no light on the individual and the HIDEN and a warning or alarm indication of exceeding a pre-determined HIDEN warning or alarm is shown by display and/or other visible or audio means to at least one person responsible for the individual's safety. For example, a coach or sports teacher can have a mobile app on a smart phone that monitors the HIDEN for each player in a sports activity. With wireless connectivity and both wired and wireless networking commonly available, a school nurse and/or school principle could also be notified that a student has exceeded an individual pre-determined risk assessment threshold for that student at about the same time the coach or teacher is notified.

In some embodiments, with the cost of electronics generally falling each year, it is also contemplated that a toddler or young child, such as, for example a pre-school age child, could wear head gear which can alert a parent of a risk assessment and/or a risk assessment that exceeds a predetermined threshold. Such relatively inexpensive systems could also be worn by children engaging in sports activities or rough play outside of an organized school or athletic event. Beyond exceptionally sensitive or at-risk children, such child monitoring outside of school and organized sports activities probably need not be done to excess.

In Summary: A system to assess risk of changes to brain white matter based on a head impact dose equivalent number includes a sensor system adapted to directly or indirectly measure an energy of each impact to at least one individual that causes a repetitive head impact (RHI). The at least one individual belongs to a sub-population. A clock means is configured to provide a time. A computer is communicatively coupled to the sensor system or to a non-volatile memory having stored thereon data from the sensor system to estimate an energy of each RHI event, and communicatively coupled to the clock means to associate thereto each energy of each RHI event a RHI time stamp and to record a time stamped energy for each RHI event. A head impact dose equivalent number (HIDEN) process runs on the computer. The HIDEN process calculates a HIDEN for a most recent RHI event based on the energy of the most recent RHI event, a time of the most recent RHI, and all previously recorded RHI events available in a non-volatile memory. Each RHI event of all previously recorded RHI events is time weighted by the time between each of the all previously recorded RHI events and the time of the most recent RHI. A sub-population function process runs on the computer or on another computer communicatively coupled to the computer. The sub-population function process is configured to calculate a risk assessment number based on the sub-population to which the at least one individual belongs and the HIDEN for the most recent RHI event. A risk assessment notification means is communicatively coupled to the computer or to another computer, the risk assessment notification means configured to provide a notification of the risk assessment number.

Another exemplary embodiment: Using the same concepts described hereinabove, and also based on the 2011 playing season data, another exemplary embodiment uses a slightly different nomenclature. A similar secondary analysis was made for DTI and helmet impact data collected on ten Division III collegiate football players during the 2011 season. All subjects underwent DTI scanning before the start of the football season and within one week of the end of the football season. Helmet impacts were recorded at each practice and game using helmet-based accelerometers, which computed five helmet-based impact metrics (HIMs) for each hit: linear acceleration (LA), rotational acceleration (RA), Gadd Severity Index (GSI), Head Injury Criterion (HIC15), and Head Impact Technology severity profile (HITsp). All HIMs were analyzed using five methods of summary: peak and mean (non-cumulative measures), season sum-totals (cumulative unweighted measures), and season sum-totals weighted for time between hits (TBH), the interval of time from hit to post-season DTI assessment (TUA), and both TBH and TUA combined. Summarized HIMs were correlated to statistically significant changes in fractional anisotropy (FA) using bivariate correlational and multivariable correlational analyses. The resulting $R^2$ values were averaged in each of the five summary method groups and compared using one-way ANOVA followed by Tukey post-hoc tests for multiple comparisons.

The total head hits for the season ranged from 431 to 1,850. None of the athletes suffered a clinically evident concussion during the study period. The mean $R^2$ value for the correlations using cumulative HIMs weighted for both TUA and TBH combined (0.51±0.03) was significantly greater than the mean $R^2$ value for correlations using non-cumulative HIMs (vs 0.19±0.04, $p<0.0001$), unweighted cumulative HIMs (vs 0.27+0.03, $p<0.0001$), and cumulative HIMs weighted for TBH alone (vs 0.34±0.02, $p<0.001$). $R^2$ values for weighted cumulative HIMs ranged from 0.32-0.77, with 60% of correlations being statistically significant. Cumulative GSI weighted for TBH and TUA explained 77% of the variance in the percent of white matter voxels with statistically significant (PWMVSS) increase in FA from pre-season to post-season, while both cumulative GSI and cumulative HIC15 weighted for TUA accounted for 75% of the variance in PWMVSS decrease in FA.

As described hereinabove, using the slightly different terminology, we performed a secondary analysis of DTI and helmet impact data collected on ten Division III collegiate football players during the 2011 season.

Ten active University of Rochester varsity football players from the 2011-2012 roster were asked to participate and all agreed. These athletes were chosen for the variety of positions and anticipated head impacts they would experience during the season. All subjects were >18 years of age and did not sustain a clinically diagnosed traumatic brain injury (TBI) of any severity within 2 weeks prior to the 2011 football season as determined by self-report using a previously validated survey tool. This research was approved by the Research Subjects Review Board at the University of Rochester. All subjects provided written informed consent prior to participation.

All subjects underwent DTI scanning before the start of the football season and within one week of the end of the football season. HIMs were collected at every practice and game throughout the season using Riddell Revolution IQ helmets (Riddell Corporation; Elyria, Ohio) equipped with the Head Impact Telemetry System (HITS, Simbex LLC; Lebanon, N.H.). Only impacts in which the calculated translational acceleration at the center of gravity of the player's head exceeded ten g-forces (g) were recorded for analysis. Accelerometer data were used to compute the following HIMs: LA, RA, the Gadd Severity Index (GSI), the Head Injury Criterion (HIC15), and the Head Impact Technology severity profile (HITsp).

DTI was acquired with a 3T Siemens Trio scanner using a single-shot pulsed-gradient SE-EPI sequence to measure FA and MD changes in WM. From the DTI images, voxel-wise comparisons of FA and MD were analyzed on a subject-specific basis. DTI data were analyzed using the wild bootstrapping permutation test, in which statistical significance of subject-specific voxel-wise changes in FA and MD were determined. From this output, the percentage of all WM voxels with a statistically significant change (increase or decrease) in FA and MD from preseason to the end of the football season within each subject was calculated. In our prior published analysis, changes in MD appeared to reflect the effects of physical, sports-related exertion on brain water diffusion rather than brain injury, thus, MD was not analyzed in this investigation.

For each subject, the percentage of WM voxels with a statistically significant increase in FA (PWMVSS↑FA), as well as decrease in FA (PWMVSS↓FA) from preseason to the end of the football season was calculated. The percentage of WM voxels with significant interval changes in FA was correlated to summary HIMs (LA, RA, GSI, HIC15, and HITsp) accrued over the entire season. Each HIM was summarized using peak and mean (non-cumulative measures), season sum-totals (cumulative unweighted measures), and season sum-totals weighted for time between exposure events.

We developed three methods of weighting HIMs for exposure events accrued over a season of play as described in more detail hereinbelow. The first two methods uniquely incorporate a temporal component between individual SHBs, while the third method is combination of the two.

Time Between Hits (TBH): This cumulative measure weights the HIM of each helmet hit by the number of prior hits, the magnitude of those hits, and the time between each of those prior hits and the current [index] hit. This model is based on the assumption that the effect of a single index hit on WM structure is inversely related to the interval of time between the prior hit and the index hit ($t_{n-j,d}-t_{n-i,d}$); the smaller the time interval, the greater the effect of the index hit.

In the first step of this method, the HIM value of each helmet hit ($h_{t(n-j,d)}$) was weighted by adding to its raw HIM value to the sum of the HIM values for all previous hits on that same day, each of which was multiplied by the inverse of the interval of time between that prior hit and the index hit. In the second step, the weighted HIM values for all hits accrued over the course of the football season were summed to yield a cumulative HIM value (C-HIM).

Let n represent the total number of head impacts received by an individual on day d, and let $h_{t(n-j,d)}$ represent the raw value of the HIM of the n−j th impact at time, t, on day, d. The cumulative HIM (C-HIM) weighted for TBH over a day is represented by:

$$C-HIM(d)_{TBH} = \sum_{j=0}^{n-1}\left(h_{t_{n-j,d}} + \sum_{i=1}^{n-j-1} h_{t_{n-i,d}}\left(\frac{1}{t_{n-j,d}-t_{n-i,d}}\right)\right)$$

The C-HIM weighted for TBH over a total of M days is represented by:

$$C-HIM(M)_{TBH} = \sum_{d=1}^{M}\sum_{j=0}^{n-1}\left(h_{t_{n-j,d}} + \sum_{i=1}^{n-j-1} h_{t_{n-i,d}}\left(\frac{1}{t_{n-j,d}-t_{n-i,d}}\right)\right)$$

Time Until Assessment (TUA): This cumulative measure weights the HIM of each helmet hit by the interval of time between the hit and the DTI assessment at the end of the season of play. This model is based on the assumption that DTI-measured changes in WM structure (i.e., FA) after traumatic axonal injury depend to some extent on the interval of time from the injury to the assessment of that injury using DTI. Although there is some controversy as to the direction and timing of these DTI changes in humans, in general axonal injury results acutely in axonal swelling which increases FA followed by axonal loss which enlarges inter-axonal spaces, decreasing FA.

In the first step of this method, the HIM value of each helmet hit was weighted by multiplying its raw value ($h_{t(i,d)}$) at time, t, on day, d, by the inverse of the time between the index hit ($t_d$) and the post-season DTI assessment ($t_D$). In the second step, the weighted HIM values for all hits accrued over the course of the football season were summed to yield a cumulative HIM value (C-HIM). This is represented by the following:

$$C-HIM(d)_{TUA} = \sum_{i=1}^{n}\left(\frac{h_{t_{i,d}}}{\max(t_D - t_d, 1)}\right)$$

The cumulative HIM (C-HIM) weighted for the TUA over a total of M days is represented by:

$$C-HIM(M)_{TUA} = \sum_{d=1}^{M}\left(\sum_{i=1}^{n}\frac{h_{t_{i,d}}}{\max(t_D - t_d, 1)}\right)$$

Time between hits and time until assessment combined (TBH+TUA): Cumulative measures weighted for both the interval of time between hits and the interval of time from hit to post-season assessment include properties from the two individual models, and are described as follows for single day:

$$C-HIM(d)_{TBH+TUA} = \sum_{j=0}^{n-1}\left(\left(h_{t_{n-j,d}} + \sum_{i=1}^{n-j-1} h_{t_{n-i,d}}\left(\frac{1}{t_{n-j,d}-t_{n-i,d}}\right)\right)\frac{1}{\max(t_D - t_d, 1)}\right)$$

The cumulative HIM (C-HIM) weighted for TBH and TUA combined over a total of M days is represented by:

$$C-HIM(M)_{TBH+TUA} = \sum_{d=1}^{M}\left(\sum_{j=0}^{n-1}\left(\left(h_{t_{n-j,d}} + \sum_{i=1}^{n-j-1} h_{t_{n-i,d}}\left(\frac{1}{t_{n-j,d}-t_{n-i,d}}\right)\right)\frac{1}{\max(t_D - t_d, 1)}\right)\right)$$

Thus, each HIM was summarized in six ways; peak and mean (non-cumulative measures), unweighted cumulative measures, and cumulative measures weighted for TBH, TUA, and TBH+TUA combined. For the purposes of comparative analysis, correlations using peak and mean HIMs were combined into a single 'non-cumulative' group, yielding five methods of summarizing HIMs (MS-HIMs). Summarized HIMs were correlated to DTI changes using bivariate correlational (BC) and multivariable correlational (MVC) analyses, except for peak and mean HIMs, where only BC was used.

BCs were estimated using the Spearman rank correlation test for each of the five HIMs. This test calculates rho ($\rho$) values which, when squared, provide a crude estimate of the fit of the model. This allows a more direct comparison to the multivariable models. MVC were estimated using the generalized linear model. A polynomial (quadratic) regression analysis was performed for all four of the cumulative HIM summary methods to account for (a) the univariate distributions of the cumulative metrics and DTI changes, (b) the expected curvilinear bivariate associations between DTI changes and cumulative impact metrics, and (c) the potential for non-monotonicity in the curvilinear associations between DTI changes and cumulative impact metrics. A multiple $R^2$ value was calculated for all correlations to provide an estimate of the variation in DTI change over one season of play explained by the HIM.

Thus, each of the five HIMs (LA, RA, GSI, HIC, and HITsp), were summarized in five ways and correlated to two types of DTI changes (PWMVSS↑FA and PWMVSS↓FA). For four of the five MS-HIMs, these correlations were performed using BC and MVC, yielding 20 correlations. But for peak and mean, only BC was used, yielding 10 correlations each, but because they were combined into a single group for the purposes of comparison, this group had 20 correlations as well. The $R^2$ values from the 20 correlations in each of the five MS-HIM groups are presented as means±standard error (SE), and statistical significance was determined using one-way ANOVA followed by Tukey post-hoc tests for multiple comparisons. Probability values <0.05 were deemed significant. All statistical analyses were performed using SAS statistical software version 9.3 (SAS Institute Inc., Cary, N.C., USA). All graphs were created using GraphPad Prism for Windows version 5.04 (GraphPad Software; La Jolla, Calif., USA).

Results: Mean age at enrollment of the ten athlete subjects was 20.7 years; all were male. Total head hits for the season ranged from 431 to 1,850. None of the athletes suffered a clinically evident concussion during the study period.

Figure 17:
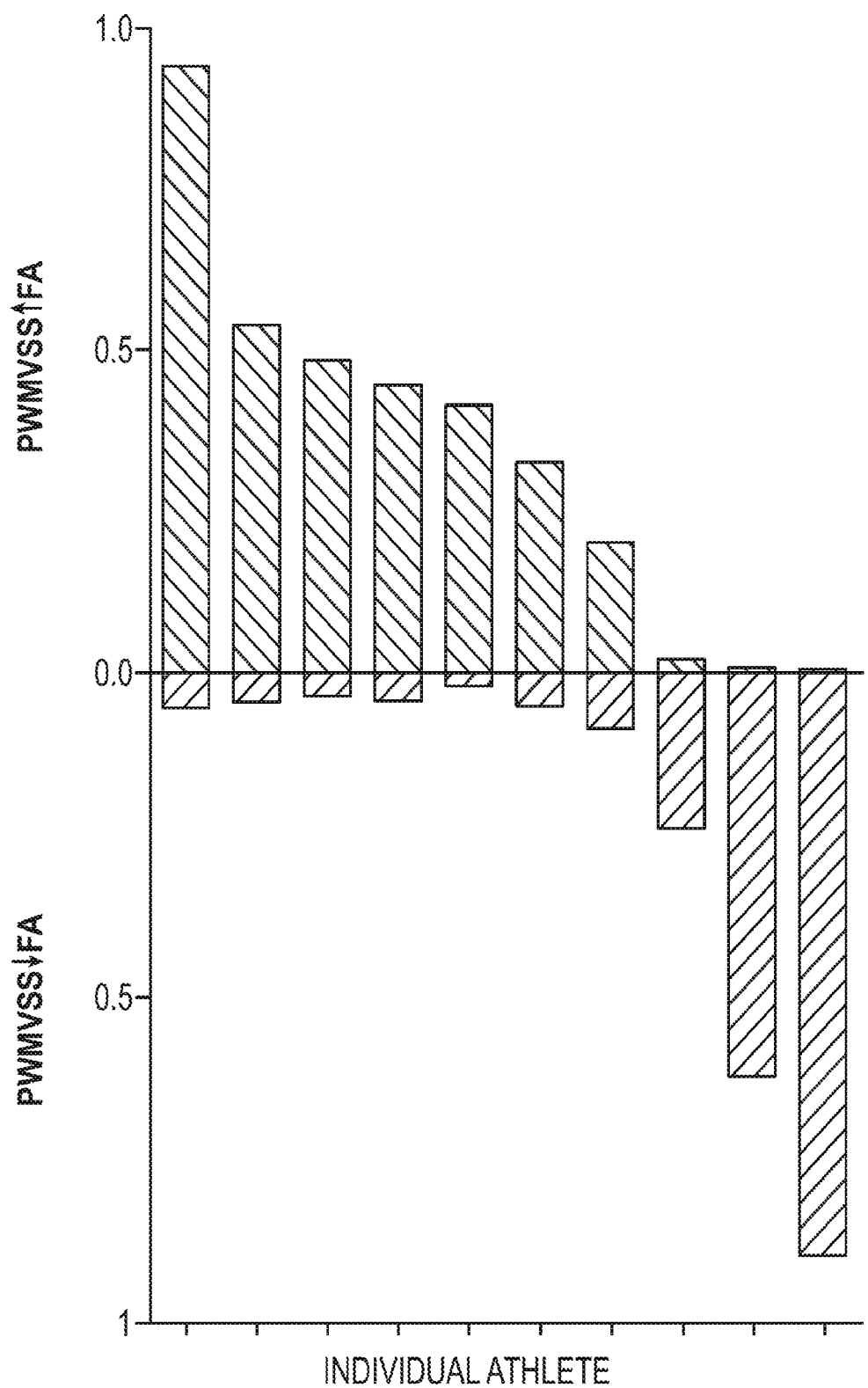
FIG. 17 shows a bar graph of subject-specific changes in PWMVSS↓FA and PWMVSS↑FA.

Changes in FA on DTI: At the end of the football season, PWMVSS↑FA ranged from 0.01% to 0.94%, and the PWMVSS↓FA ranged from 0.02% to 0.89% (FIG. 17). In FIG. 17, subject-specific changes in FA from pre-season to post-season. Bars represent the percentage of white matter voxels in each individual subject with significantly increased (grey) and decreased (black) FA over the specified time interval.

Helmet Impact Metrics: Among the ten athletes, mean LA per hit ranged from 26.91 g (offensive tackle) to 37.53 g (linebacker), while mean RA per hit ranged from 1691.95 rad/sec2 (defensive lineman) to 2071.71 rad/sec2 (linebacker). Peak LA ranged from 98.2 g (defensive lineman) to 179.5 g (running back) while peak RA per hit ranged from 7611.6 rad/sec2 (defensive lineman) to 16660.6 rad/sec2 (running back). Non-cumulative measures for GSI, HIC and HITsp, as well as cumulative summaries for all five impact metrics, are shown in the table of FIG. 16.

Figure 18:
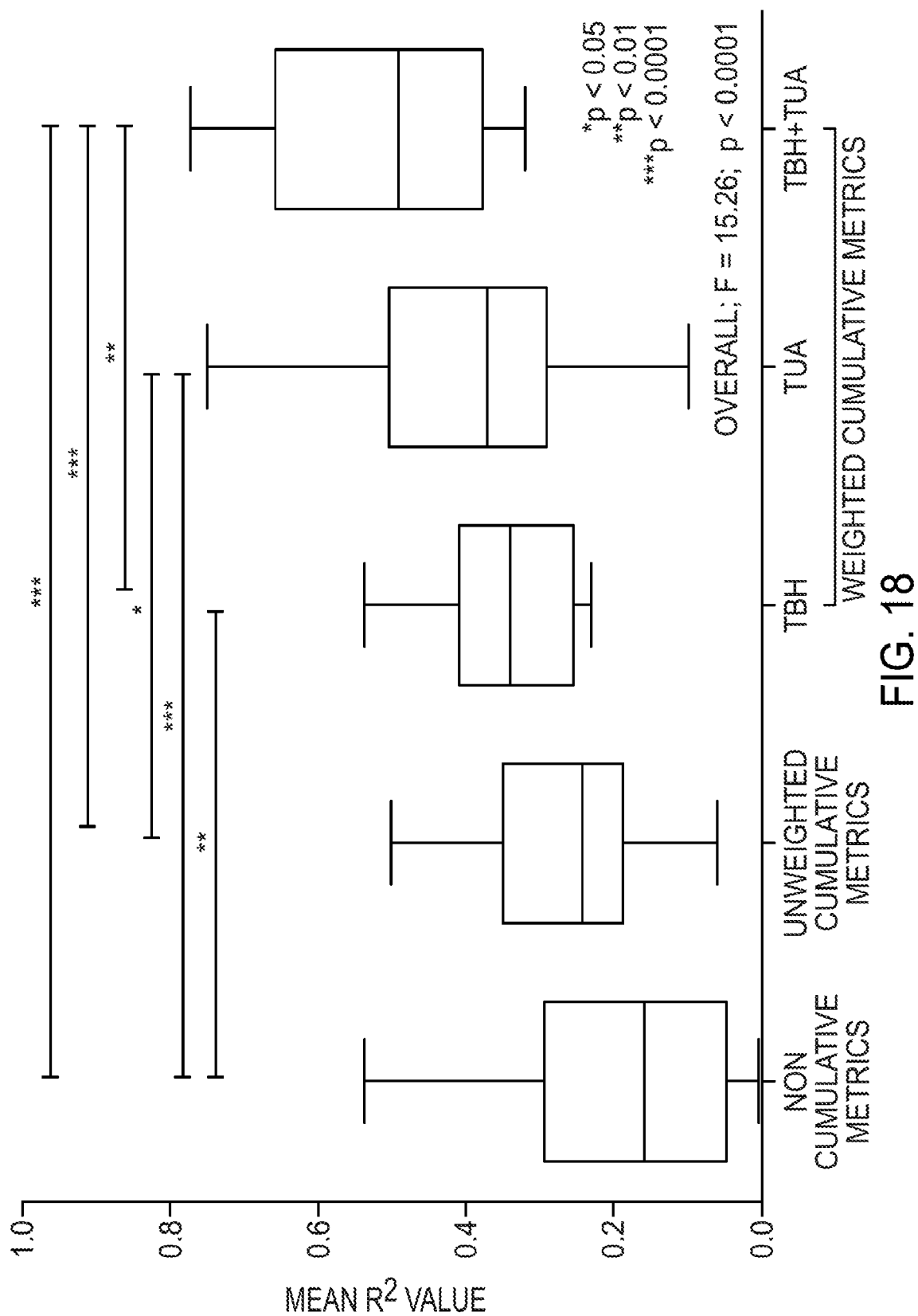
FIG. 18 shows a graph of mean $R^2$ values for the correlation of changes in FA with 5 methods of summarizing helmet impact metrics.

Correlation of Helmet Impact Metrics to Changes in FA on DTI: Weighting HIMs markedly improved the correlations to DTI changes. Among the five MS-HIM groups, a between-groups one-way ANOVA revealed a significant effect of group (F4,99=15.46, p<0.0001), FIG. 18. In FIG. 18, box and whisker plot of mean R2 values for each group of MS-HIM (n=20 per group). Horizontal lines within each box represent the mean, and bars extend to the minimum and maximum R2 value within each group.

This effect was most pronounced when HIMs were weighted for both TBH and TUA combined. The mean $R^2$ value for the 20 correlations using cumulative HIMs weighted for both TUA and TBH combined (0.51±0.03) was significantly greater than the mean $R^2$ value for correlations using non-cumulative HIMs (vs 0.19+0.04; p<0.0001), non-weighted cumulative HIMs (vs 0.27±0.03; p <0.0001), and cumulative HIMs weighted for TBH alone (vs 0.34±0.02; p<0.001). However, there was no significant difference when compared to cumulative HIMs weighted for TUA alone (vs 0.40±0.04, p=0.15). The 20 $R^2$ values in the TBH and TUA combined group ranged from 0.32-0.77, with 60% of correlations with DTI being statistically significant (FIG. 14). However, weighting HIMs for TBH alone and TUA alone also significantly improved correlation to DTI changes, relative to unweighted cumulative and non-cumulative measures. Mean $R^2$ value for correlations using HIMs weighted for TBH alone (0.34+0.02) were significantly greater than mean $R^2$ value for correlations using non-cumulative HIMs (vs 0.19+0.04, p<0.001). Likewise, mean $R^2$ value for correlations using HIMs weighted for TUA alone (0.40+0.04) were significantly greater than mean $R^2$ value for correlations using non-cumulative HIMs (vs 0.19+0.04, p<0.001) and unweighted cumulative HIMs (vs 0.27+0.03, p<0.05). There was no significant difference in mean $R^2$ values for HIMs weighted for TBH alone compared to TUA alone (0.34+0.02 vs 0.40+0.04)

This stepwise improvement in $R^2$ values that comes with using weighted cumulative HIMS is best exemplified by the relationship between HIC15 and PWMVSS↑FA (FIG. 13). In FIG. 13, model R2 values from correlations with pre-season to post-season changes in FA and each summary HIM plotted on the y-axis. Significant model R2 values are noted with an asterisk. The summary HIM and correlation type (BC or MVC) are noted in the legend. LA (linear acceleration), RA (rotational acceleration), Gadd Severity Index (GSI), Head Injury Criterion (HIC15), Head Impact Technology severity profile (HITsp), TBH (time between hits), TUA (time until DTI assessment, BC (bivariate correlation), MVC (multivariable correlation).

The model $R^2$ value was 0.03 using peak HIC15, 0.24 using cumulative non-weighted HIC15, 0.37 using cumulative HIC15 weighted for TBH, 0.45 using cumulative HIC15 weighted for TUA, and 0.71 using cumulative HIC15 weighted for both TUA and TBH combined.

Correlation of Helmet Impact Metrics to PWMVSS↑FA: In general, improvements in $R^2$ values using weighted cumulative HIMs were larger and more prevalent among correlations to PWMVSS↑FA than among correlations to PWMVSS↓FA. Fourteen (28%) correlations with PWMVSS↑FA were statistically significant (FIG. 13); all were negative correlations (FIG. 14). IN the table of FIG. 20, model R and R2 values and the corresponding significance level from correlations with pre-season to post-season changes in FA and each summary HIM are listed. The summary HIM and correlation type (BC or MVC) are noted in the legend. LA (linear acceleration), RA (rotational acceleration), Gadd Severity Index (GSI), Head Injury Criterion (HIC15), Head Impact Technology severity profile (HITsp), TBH (time between hits), TUA (time until DTI assessment, BC (bivariate correlation), MVC (multivariable correlation).

The highest model $R^2$ value (0.77, p<0.001) was observed with cumulative GSI weighted for TBH and TUA combined, although the correlation to cumulative HIC15 (0.71, p=0.001) weighted for TBH and TUA combined was nearly as strong.

Correlation of Helmet Impact Metrics to PWMVSS↓FA: Eleven (22%) correlations with PWMVSS↓FA were statistically significant (FIG. 13); all were positive correlations (FIG. 14). The highest model $R^2$ value (0.75, p<0.001) was observed with cumulative GSI and cumulative HIC15 weighted for TUA alone. No HIMs involving RA or HITsp were significantly correlated to PWMVSS↓FA.

It is understood that software and/or firmware of the system and method for risk management system for mitigating an individual's brain white matter change or injury resulting from repetitive head impact (RHI) can be provided on a computer readable non-transitory storage medium as non-transitory data. Also, recent RHI time stamped data and head impact dose equivalent numbers (HIDENs) are also typically stored on a computer readable non-transitory storage medium as non-transitory data. A computer readable non-transitory storage medium as non-transitory data storage includes any data stored on any suitable media in a non-fleeting manner Such data storage includes any suitable computer readable non-transitory storage medium, including, but not limited to hard drives, non-volatile RAM, SSD devices, CDs, DVDs, etc.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A system to assess risk of changes to brain white matter based on a head impact dose equivalent number comprising:
 a sensor system adapted to directly or indirectly measure an energy of each impact to at least one individual that causes a repetitive head impact (RHI), said at least one individual belonging to a sub-population;
 a clock means configured to provide a time;
 a computer communicatively coupled to said sensor system or to a non-volatile memory having stored thereon data from said sensor system to estimate an energy of each RHI event, and communicatively coupled to said clock means to associate thereto each energy of each RHI event a RHI time stamp and to record a time stamped energy for each RHI event;
 a head impact dose equivalent number (HIDEN) process running on said computer, said HIDEN process to calculate a HIDEN for a most recent RHI event based on an energy of said most recent RHI event, a time of said most recent RHI, and all previously recorded RHI events available in a non-volatile memory, each RHI event of all previously recorded RHI events time weighted by the time between each of said all previously recorded RHI events and said time of said most recent RHI;
 a sub-population function process running on said computer or on another computer communicatively coupled to said computer, said sub-population function process configured to calculate a risk assessment number based on said sub-population to which said at least one individual belongs and said HIDEN for said most recent RHI event; and
 a risk assessment notification means to assess risk of changes to brain white matter communicatively coupled to said computer or to said another computer, said risk assessment notification means configured to provide a notification of said risk assessment number.

2. The system to assess risk of claim 1, wherein said head impact dose equivalent number (HIDEN) process is further weighted by the time to an end of a season or predetermined activity period.

3. The system to assess risk of claim 1, wherein said notification means further provides each new risk assessment number in about real-time.

4. The system to assess risk of claim 1, wherein said head impact dose equivalent number (HIDEN) process runs an equation:

$$C - HIM(d)_{TUA} = \sum_{i=1}^{n}\left(\frac{h_{t_{i,d}}}{\max(t_D - t_d, 1)}\right)$$

where a helmet impact measure (HIM) value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed to yield a cumulative HIM value (C-HIM).

5. The system to assess risk of claim 1, wherein said head impact dose equivalent number (HIDEN) process runs an equation:

$$C - HIM(M)_{TUA} = \sum_{d=1}^{M}\left(\sum_{i=1}^{n}\frac{h_{t_{i,d}}}{\max(t_D - t_d, 1)}\right)$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed to yield a cumulative HIM (C-HIM) weighted for the TUA over a total of M days.

6. The system to assess risk of claim 1, wherein said head impact dose equivalent number (HIDEN) process runs an equation:

$$C - HIM(d)_{TBH+TUA} = \sum_{j=0}^{n-1}\left(\left(h_{t_{n-j,d}} + \sum_{i=1}^{n-j-1} h_{t_{n-i,d}}\left(\frac{1}{t_{n-j,d} - t_{n-i,d}}\right)\right)\frac{1}{\max(t_D - t_d, 1)}\right)$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed and cumulative measures are weighted for both the interval of time between hits and the interval of time from hit to post-season assessment include properties from the two individual models, and are described as follows for single day to yield a time between hits and a time until assessment combined (TBH+TUA).

7. The system to assess risk of claim 1, wherein said head impact dose equivalent number (HIDEN) process runs an equation:

$$C - HIM(M)_{TBH+TUA} = \sum_{d=1}^{M}\left(\sum_{j=0}^{n-1}\left(\left(h_{t_{n-j,d}} + \sum_{i=1}^{n-j-1} h_{t_{n-i,d}}\left(\frac{1}{t_{n-j,d} - t_{n-i,d}}\right)\right)\frac{1}{\max(t_D - t_d, 1)}\right)\right)$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed and cumulative measures are weighted for both the interval of time between hits to yield a cumulative HIM (C-HIM) weighted for TBH and TUA combined over a total of M days.

8. The system to assess risk of claim 1, wherein said head impact dose equivalent number (HIDEN) process runs an equation:

$$HIDEN_n = ht_n + \sum_{i=1}^{n-1} ht_{n-i}\left[\frac{1}{t_n - t_{n-i}}\right]$$

where, $HIDEN_n$ is the head impact dose equivalent number following a most recent head impact, $ht_n$ is a magnitude of the energy of the most recent head impact, $ht_{n-i}$ is the magnitude of the energy of an n–i previous head impact, n is a total number of RHI, $t_n$ is the time of the most recent head impact, and $t_{n-i}$ is a time between a most recent RHI event n and an $i^{th}$ RHI event.

9. The system to assess risk of claim 1, wherein said head impact dose equivalent number (HIDEN) process runs an equation:

$$HIDEN_n = \sum_{i=1}^{n} \frac{ht_i}{\max(1, t_S - t_i)} + \sum_{i=1}^{n-1} \frac{ht_{n-i}\left[\frac{1}{t_n - t_{n-i}}\right]}{\max(1, t_S - t_{n-i})}$$

where, $HIDEN_n$ is the head impact dose equivalent number following a most recent head impact, now also as a function of time into a playing season (or, equivalent period of time), $ht_i$ is a magnitude of the energy of the most recent head impact, $ht_{n-i}$ is a magnitude of the energy of an n–i previous head impact, n is a total number of RHI this calculation, $t_s$ is a time to an end of a current playing season, and $t_i$ is the time of the most recent head impact.

10. The system to assess risk of claim 1, wherein said sensor system comprises at least one accelerometer or at least one gyro.

11. The system to assess risk of claim 1, wherein said sensor system comprises at least one camera to provide at least one image of an impact to said individual and wherein said at least one image of an impact is converted or used to estimate to an energy value of an RHI corresponding to said impact.

12. The system to assess risk of claim 1, wherein said computer is communicatively coupled to a non-volatile memory having stored thereon a pre-recorded video footage data from one or more video cameras of said sensor system to estimate an energy of each RHI event.

13. The system to assess risk of claim 1, wherein said system to assess risk comprises a wireless sensor system communicatively coupled to said computer.

14. The system to assess risk of claim 1, wherein said system to assess risk is disposed in a head gear comprising said sensor system, said computer, said clock, and said head impact dose equivalent number (HIDEN) process running on said computer, and said system to assess risk is wirelessly coupled to another computer or display device which displays a most recent HIDEN for each individual.

15. The system to assess risk of claim 1, wherein said sensor system comprises at least one sensor disposed in a mouth guard.

16. The system to assess risk of claim 1, wherein said sensor system comprises at least one sensor disposed in a skin patch or a sub-dermal implant.

17. The system to assess risk of claim 1, wherein said sensor system comprises at least one sensor disposed in a dental filling or dental implant.

18. The system to assess risk of claim 1, wherein said sensor system comprises at least one sensor disposed in an ear insert.

19. The system to assess risk of claim 1, wherein said sensor system comprises at least one sensor disposed in an ocular device.

20. The system to assess risk of claim 19, wherein said ocular device comprises at least one sensor disposed in a contact lens or eye glasses.

21. The system to assess risk of claim 1, wherein said sensor system comprises at least one sensor worn on said at least one individual's body other than as part of a head gear.

22. The system to assess risk of claim 21, wherein said head gear comprises a helmet or a skull cap.

23. A method to assess risk of changes to brain white matter based on a head impact dose equivalent number comprising:
providing a sensor system adapted to directly or indirectly measure an energy of each impact to at least one individual that causes a repetitive head impact (RHI), said at least one individual belonging to a sub-population, a clock means configured to provide a time, and at least one computer communicatively coupled to said sensor system or to a non-volatile memory having stored thereon data from, and communicatively coupled to said clock means, and a notification means communicatively coupled to said at least one computer;
estimating a directly or indirectly measure an energy of each impact to at least one individual that causes a repetitive head impact (RHI), said at least one individual belonging to a sub-population;
calculating a head impact dose equivalent number (HIDEN) process running on said computer, said HIDEN process to calculate a HIDEN for a most recent RHI event based on an energy of said most recent RHI event, a time of said most recent RHI, and all previously recorded RHI events available in a non-volatile memory, each RHI event of all previously recorded RHI events time weighted by the time between each of said all previously recorded RHI events and said time of said most recent RHI;
calculating a risk assessment number using a sub-population function based on said sub-population to which said at least one individual belongs and said HIDEN for said most recent RHI event; and
notifying at least one other individual by use of said notification means of said risk assessment number.

24. The method to assess risk of claim 23, wherein said step of calculating a HIDEN is further weighted by the time to an end of a season or predetermined activity period.

25. The method for risk management system of claim 23, wherein said step of calculating a HIDEN comprises calculating a HIDEN based an equation:

$$C - HIM(d)_{TUA} = \sum_{i=1}^{n} \left(\frac{h_{t_{i,d}}}{\max(t_D - t_d, 1)}\right)$$

where a helmet impact measure (HIM) value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed to yield a cumulative HIM value (C-HIM).

26. The method for risk management system of claim 23, wherein said step of calculating a HIDEN comprises calculating a HIDEN based an equation:

$$C\text{-}HIM(M)_{TUA} = \sum_{d=1}^{M}\left(\sum_{i=1}^{n} \frac{h_{t_{i,d}}}{\max(t_D - t_d, 1)}\right)$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed to yield a cumulative HIM (C-HIM) weighted for the TUA over a total of M days.

27. The method for risk management system of claim 23, wherein said step of calculating a HIDEN comprises calculating a HIDEN based an equation:

$$C\text{-}HIM(d)_{TBH+TUA} = \sum_{j=0}^{n-1}\left(\left(h_{t_{n-j,d}} + \sum_{i=1}^{n-j-1} h_{t_{n-i,d}}\left(\frac{1}{t_{n-j,d} - t_{n-i,d}}\right)\right)\frac{1}{\max(t_D - t_d, 1)}\right)$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed and cumulative measures are weighted for both the interval of time between hits and the interval of time from hit to post-season assessment include properties from the two individual models, and are described as follows for single day to yield a time between hits and a time until assessment combined (TBH+TUA).

28. The method for risk management system of claim 23, wherein said step of calculating a HIDEN comprises calculating a HIDEN based an equation:

$$C\text{-}HIM(M)_{TBH+TUA} = \sum_{d=1}^{M}\left(\sum_{j=0}^{n-1}\left(\left(h_{t_{n-j,d}} + \sum_{i=1}^{n-j-1} h_{t_{n-i,d}}\left(\frac{1}{t_{n-j,d} - t_{n-i,d}}\right)\right)\frac{1}{\max(t_D - t_d, 1)}\right)\right)$$

where a HIM value of each helmet hit is weighted by multiplying its raw value ($ht_{i,d}$) at a time, t, on a day, d, by an inverse of a time between the index hit ($t_d$) and a post-season DTI assessment ($t_D$), and a weighted HIM values for all hits accrued over the course of the football season are summed and cumulative measures are weighted for both the interval of time between hits to yield a cumulative HIM (C-HIM) weighted for TBH and TUA combined over a total of M days.

29. The method for risk management system of claim 23, wherein said step of calculating a HIDEN comprises calculating a HIDEN based an equation:

$$HIDEN_n = ht_n + \sum_{i=1}^{n-1} ht_{n-i}\left[\frac{1}{t_n - t_{n-i}}\right]$$

where, $HIDEN_n$ is the head impact dose equivalent number following a most recent head impact, $ht_n$ is a magnitude of the energy of the most recent head impact, $ht_{n-i}$ is a magnitude of the energy of an n−i previous head impact, n is a total number of RHI, $t_n$ is the time of the most recent head impact, and $t_{n-i}$ is a time between a most recent RHI event n and an $i^{th}$ RHI event.

30. The method to assess risk of claim 23, wherein said step of calculating a HIDEN comprises calculating a HIDEN based an equation:

$$HIDEN_n = \sum_{i=1}^{n} \frac{ht_i}{\max(1, t_S - t_i)} + \sum_{i=1}^{n-1} \frac{ht_{n-i}\left[\frac{1}{t_n - t_{n-i}}\right]}{\max(1, t_S - t_{n-i})}$$

where, $HIDEN_n$ is the head impact dose equivalent number following a most recent head impact, now also as a function of time into a playing season (or, equivalent period of time), $ht_i$ is a magnitude of the energy of the most recent head impact, $ht_{n-i}$ is a magnitude of the energy of an n−i previous head impact, n is a total number of RHI this calculation, $t_s$ is a time to an end of a current playing season, and $t_i$ is the time of the most recent head impact.

* * * * *